(12) United States Patent
Stieber et al.

(10) Patent No.: US 8,436,186 B2
(45) Date of Patent: May 7, 2013

(54) THIAZOLYL PIPERIDINE DERIVATIVES

(75) Inventors: Frank Stieber, Heidelberg (DE); Timo Heinrich, Gross-Umstadt (DE); Dirk Wienke, Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 13/000,573

(22) PCT Filed: May 28, 2009

(86) PCT No.: PCT/EP2009/003817
§ 371 (c)(1),
(2), (4) Date: Dec. 21, 2010

(87) PCT Pub. No.: WO2009/156041
PCT Pub. Date: Dec. 20, 2009

(65) Prior Publication Data
US 2011/0105505 A1    May 5, 2011

(30) Foreign Application Priority Data
Jun. 23, 2008  (DE) .......................... 10 2008 029 734

(51) Int. Cl.
*C07D 211/06*    (2006.01)
*A61K 31/55*    (2006.01)

(52) U.S. Cl.
USPC ......................................... 546/205; 514/319

(58) Field of Classification Search .................. 546/205; 514/319
See application file for complete search history.

(56) References Cited

U.S. PATENT DOCUMENTS

2007/0043083 A1    2/2007    Nettekoven et al.
2009/0143413 A1    6/2009    Adams et al.

FOREIGN PATENT DOCUMENTS

WO    WO 2007/020213        *    2/2007
WO    WO 2007/020213 A2         2/2007
WO    WO 2007/064553 A2         6/2007

OTHER PUBLICATIONS

Kerns et al, Drug-like Properties: Concepts, Structure Design and Methods: from ADME to Toxicity Optimization, (Elsevier, 2008) pp. 92-93.*
Goosen et al., Pharmaceutical Research vol. 19, No. 1, Jan. 13-19, 2002.*
Edwards, J. Med. Chem. 39 (1996), pp. 1112-1124.*
Rautio, Eur. J. Pharm. Sci. 11:157-163 (2000).*
Fourie, International Journal of Pharmaceutics vol. 279, Issues 1-2, Jul. 26, 2004, pp. 59-66.*
International Search Report of PCT/EP2009/003817, Date of Completion Mar. 17, 2010, Date of Mailing Mar. 25, 2010.
Tervo, A.J. et al.: "Discovering Inhibitors of Human Sirtuin type 2: Novel Structural Scaffolds," Journal of Medicinal Chemistry, Bd. 49, Nr. 24, Feb. 9, 2006, Seiten 7239-7241, XP002573020.

* cited by examiner

*Primary Examiner* — John Mabry
(74) *Attorney, Agent, or Firm* — Millen, White, Zelano & Branigan, P.C.

(57) ABSTRACT

Compounds of the formula (I), in which $R^1$, $R^2$, $R^3$, $R^4$, $R^5$, $R^6$, $R^9$, $R^{10}$, $R^{11}$, Q and W have the meanings indicated in Claim 1, and precursors thereof are inhibitors of sphingosine kinase and can be employed, inter alia, for the treatment of tumors.

4 Claims, No Drawings

THIAZOLYL PIPERIDINE DERIVATIVES

BACKGROUND OF THE INVENTION

The invention was based on the object of finding novel compounds having valuable properties, in particular those which can be used for the preparation of medicaments.

The present invention relates to compounds and to the use of compounds for the treatment of diseases which are associated with an increase in the sphingosine phosphate level, furthermore to pharmaceutical compositions which comprise these compounds.

In detail, the present invention relates to compounds of the formula I, which preferably inhibit the enzyme sphingosine kinase 1, which regulates the sphingosine phosphate level by phosphorylation of sphingosine, to compositions which comprise these compounds, and to methods for the use thereof for the treatment of diseases and complaints, such as cancer, tumour formation, growth and spread, arteriosclerosis, eye diseases, choroidal neovascularisation and diabetic retinopathy, inflammatory diseases, arthritis, neurodegeneration, restenosis, heart diseases, wound healing or transplant rejection. In particular, the compounds according to the invention are suitable for the therapy of cancer diseases.

Sphingosine phosphate belongs to the molecule family of the sphingolipids, which, besides their role as structural building blocks of cell membranes, also exert important functions as extra- and intracellular signal molecules. Sphingosine phosphate (S1P) is formed in the cell from sphingomyelin, which initially breaks down to form ceramide and sphingosine, and the latter is phosphorylated by sphingosine kinases. Of the two sphingosine kinases identified to date, sphingosine kinase 1 (SphK1) is ascribed the greater importance in the formation of S1P in the serum (Zemann et al., 2006 Blood Vol 107 page 1454). While ceramide and sphingosine induce cell death and cell growth inhibition (Kolesnick 2002, J Clin Invest Vol 110, page 3; Ogretmen et al. 2004 Nat Rev Cancer Vol 4, page 604), sphingosine phosphate has an opposite effect on the cell and increases the resistance to apoptosis, cell growth and the discharge of messenger substances, which promote perfusion of the tissue and thus also of tumours (Cuvilier et al. 1996, Nature Vol 381, page 800; Perez et al. 1997, Nat Med Vol 3, page 1228). The ratio of ceramide and sphingosine on the one hand and S1P on the other is consequently decisive for cell growth, and inhibition of SphK 1 can thus not only suppress the formation of the growth-promoting sphingosine phosphate, but also increase the cellular concentration of the growth-inhibiting molecules ceramide and sphingosine.

A multiplicity of cellular effects which are triggered by S1P is promoted by secretion of S1P and binding thereof to to date 5 different G-protein-coupled receptors (known as $S1P_{1-5}$). Signal propagation in turn takes place via various G-proteins ($G_i$, $G_q$, $G_{12/13}$), meaning that a number of different cellular signailing pathways, such as, for example, ERK or PI3K, which are particularly important in cancer formation and growth, are activated. In addition, an increasing number of publications shows that S1P is an important factor in tumoral angiogenesis. Angiogenesis is an important process in tumour growth, by means of which blood vessels are re-formed starting from already existing ones and the supply of the tumour with nutrients is thus ensured. For this reason, inhibition of angiogenesis is an important starting point for cancer and tumour therapy. (Folkman, 2007, Nature Reviews Drug Discovery Vol. 6, page 273-286). S1P stimulates chemotactic movement of endothelial cells and induces differentiation to give multicellular structures, both early steps in the formation of new blood vessels (Lee et al. 1999 Biochem Biophys Res Commun Vol 264 page 325; Argraves et al. 2004 J Biol Chem Vol 279 page 50580). In addition, S1P promotes the migration of endothelial precursor cells originating from bone marrow to neovascular initiation sites (Annabi et al. 2003 Exp Hematology Vol 31 page 640) and trans-activates the receptor of VEGF, one of the most important proangiogenic factors, in particular in tumour biology (Tanimoto et al. 2002 J Biol Chem Vol 277 page 42997; Endo et al. 2002 J Biol Chem Vol 277 page 23747). Direct evidence of the activity of S1P in tumour angiogenesis has been provided by experiments with an antibody which binds specifically to S1P. The S1P antibody inhibited the migration and vascularisation of endothelial cells in vitro, blocked the S1P-dependent secretion of proangiogenic factors, such as VEGF, IL-8 and IL-6, in vitro and in vivo and significantly reduced the growth of tumour models of the breast, lung and ovaries in mouse xenograft experiments (Visentin 2006 Cancer Cell Vol 9 page 225).

In addition, S1P also has intracellular functions, such as, for example, the activation of the transcription factor NF-κB, which plays a major role in apoptosis resistance of cancer cells (Xia et al. 2002 J Biol Chem Vol 277 page 7996). However, the intracellular interaction partners of S1P have not yet been identified.

It follows from this that, in contrast to a likewise conceivable intervention with the cancer-promoting action of S1P by pharmacological blockade of the extracellular receptors, inhibition of the enzyme SphK1, which is responsible for S1P formation, has the advantage of thus also suppressing the intracellular activities of S1P. This approach is supported by investigations by Xia et al. (2000 Curr Biol Vol 10 page 1527), which show that non-tumorigenic fibroblasts are transformed by ectopic expression of SphK1 and can form tumours in mice. SphK1 can thus be classified as an oncogene. In various expression studies, increased SphK1-mRNA concentrations in tumour tissues of the brain, breast, lung, ovaries, stomach, uterus, kidneys and small and large intestine have been observed compared with healthy tissue (French et al. 2003 Cancer Research Vol. 63 page 5962; Johnson et al. 2005 J Histochem Cytochem Vol 53 page 1159; Van Brocklyn et al. 2005 J Neuropathol Exp Neurol Vol 64 page 695). In addition, increased expression of SphK1 correlates with a worse prognosis in patients with glioblastoma multiforme (Van Brocklyn et al. 2005 J Neuropathol Exp Neurol Vol 64 page 695). SphK1 has an important role in the modulation of the apoptosis of cancer cells induced by chemotherapeutic agents. Thus, overexpression of SphK1 increases the resistance of breast cancer, prostate cancer and leukaemia cells to chemotherapeutic agents, such as anthracyclines, docetaxel, camptothecin or doxorubicin (Nava et al. 2002 Exp Cell Res Vol 281 page 115; Pchejetski 2005 Cancer Res Vol 65 page 11667; Bonhoure 2006 Leukemia Vol 20 page 95). It has been shown that the increased presence of SphK1 results in a shift in the ceramide/S1P equilibrium towards S1P, which promotes apoptosis resistance. A possible mechanism here is the inhibition of the mitochondrial cytochrome C discharge by SphK1, which normally represents an early event in programmed cell death (Cuvilier et al. 2001 Blood Vol 98 page 2828; Bonhoure 2006 Leukemia Vol 20 page 95).

Conversely, specific blockade of SphK1 expression by means of siRNA in tumour cell models of various indications, such as leukaemia, breast cancer, glioblastoma or prostate cancer, enables apoptosis to be triggered or the effect of chemotherapeutic agents to be increased (Bonhoure 2006 Leukemia Vol 20 page 95; Taha et al. 2004 J Biol Chem Vol 279 page 20546; Taha et al. 2006 FASEB J Vol 20 page 482;

Van Brocklyn et al. 2005 J Neuropathol Exp Neurol Vol 64 page 695; Pchejetski 2005 Cancer Res Vol 65 page 11667).

It has been shown in a mouse model that overexpression of SphK1 triggers degenerative changes of cardiomyocytes and myocardial fibrosis, which increased with increasing age of the experimental animals. A function of the S1P signalling pathway in heart diseases is also supported by the fact that the formation of cardiovascular fibroses is strongly inhibited in mice in which the expression of the S1P3 receptor has been specifically suppressed (Takuwa 2008 Biochimica and Biophysica Acta in press). S1P also has a role in the differentiation of fibroblasts to give myofibroblasts and thus in the formation and progression of fibrotic diseases in other organs, such as, for example, the lung (Kono et al. 2007 Am J Respir Cell Mol Biol page 395).

It has been found that the compounds according to the invention cause specific inhibition of sphingosine kinase 1, but not of sphingosine kinase 2. The compounds according to the invention preferably exhibit an advantageous biological activity which can be detected in the tests described herein, for example. In such tests, the compounds according to the invention exhibit and cause an inhibiting effect, which is usually documented by $IC_{50}$ values in a suitable range, preferably in the micromolar range and more preferably in the nanomolar range.

In general, all solid and non-solid tumours can be treated with the compounds of the formula I, such as, for example, monocytic leukaemia, brain, urogenital, lymph system, stomach, laryngeal, ovarian and lung carcinoma, including lung adenocarcinoma and small-cell lung carcinoma. Further examples include prostate, pancreatic and breast carcinoma.

As discussed herein, effects of the compound according to the invention are relevant for various diseases. Accordingly, the compounds according to the invention are useful in the prophylaxis and/or treatment of diseases which are influenced by inhibition of SphK1.

The present invention therefore relates to compounds according to the invention as medicaments and/or medicament active ingredients in the treatment and/or prophylaxis of the said diseases and to the use of compounds according to the invention for the preparation of a pharmaceutical agent for the treatment and/or prophylaxis of the said diseases, and also to a method for the treatment of the said diseases comprising the administration of one or more compounds according to the invention to a patient in need of such an administration.

The host or patient can belong to any mammalian species, for example a primate species, particularly humans; rodents, including mice, rats and hamsters, rabbits, horses, cows, dogs, cats, etc. Animal models are of interest for experimental investigations, where they represent a model for the treatment of human disease.

The sensitivity of a particular cell to treatment with the compounds according to the invention can be determined by in vitro tests. Typically, a culture of the cell is combined with a compound according to the invention at various concentrations for a period of time which is sufficient to enable the active agents to lower the intracellular S1P concentration and in addition to block the secretion of angiogenesis-promoting substances or to induce cell death. For testing in vitro, cultivated cells from a biopsy sample or established cancer cell lines in which SphK1 is overexpressed can be used.

The dose varies depending on the specific compound used, the specific disease, the patient status, etc. A therapeutic dose is typically sufficient to considerably reduce the undesired cell population in the target tissue, while the viability of the patient is maintained. The treatment is generally continued until a considerable reduction has occurred, for example at least about 50% reduction in the cell burden, and can be continued until essentially no undesired cells can be detected in the body.

Use

As described in the introduction, SphK1, S1P and the cell surface receptors $S1P_{1-5}$ thereof are involved in a multiplicity of physiological and pathophysiological processes. For this reason, it can be expected that the inhibition of SphK1 by the substances described here can be utilised for therapeutic purposes in various diseases.

The formation of S1P by SphK1 and the associated shift in the ceramide/S1P equilibrium results, as stated above, in the cells proliferating to a greater extent and becoming more resistant to apoptotic stimuli. A general function of SphK1 can be derived therefrom in hyperproliferative diseases, such as cancer, psoriasis, restenosis and arteriosclerosis. The compounds of the formula I on which this invention is based and which inhibit SphK1 and thus regulate and/or modulate the S1P level, compositions which comprise these compounds, and the methods described can thus be employed for the treatment of these diseases. In general, all solid and non-solid tumours can be treated with the compounds of the formula X, such as, for example, monocytic leukaemia, brain, urogenital, lymph system, stomach, laryngeal ovarian and lung carcinoma, including lung adenocarcinoma and small-cell lung carcinoma. Further examples include prostate, pancreatic and breast carcinoma.

Besides the function in cell growth, S1P also plays a role in the neoformation of blood vessels (angiogenesis). In many disease processes, angiogenesis is either causally at the centre of the disease or has a worsening effect on the progression of the disease. In cancer events, for example, angiogenesis results in the tumour being enlarging and possibly spreading into other organs. Further diseases in which angiogenesis plays an important role are psoriasis, arthrosis, arteriosclerosis and eye diseases, such as diabetic retinopathy, age-induced macular degeneration, rubeosis iridis or neovascular glaucoma. The compounds of the formula I on which this invention is based and which inhibit SphK1 and thus regulate and/or modulate the S1P level, compositions which comprise these compounds, and the methods described can thus be employed for the treatment of these diseases.

Furthermore, SphK1 and S1P influence the proliferation, differentiation, migration and secretion of immune cells (Rosen and Goetzl 2005 Nat Rev Immunol Vol 5 page 560) and are thus involved in various functions of the immune system and in inflammatory processes. Stimulation of the immune system increases the formation and discharge of S1P in mast cells, blood platelet cells and some mononuclear phagocytes (Stunff et al. 2004 J Cell Biochem Vol 92 page 882; Olivera and Rivera 2005 j Immunol Vol 174 page 1153). The activity of SphK1 is greatly increased, in particular, by factors such as tumour necrosis factor (TNF) and crosslinking of IgG receptors (Stunff et al. 2004 J Cell Biochem Vol 92 page 882; Delon et al. 2004 J Biol Chem Vol 279 page 44763). In addition, it has been shown that SphK1 and S1P are important for the TNF-dependent formation of pro-inflammatory enzymes, such as cyclooxygenase-2 (COX-2) and nitric oxide synthase (NOS) (Pettus et al. 2003 FASEB J Vol 17 page 1411; Kwon et al. 2001 J Biol Chem Vol 276 page 10627-33). The compounds of the formula I on which this invention is based and which inhibit SphK1 and thus regulate and/or modulate the S1P level, compositions which comprise these compounds, and the methods described can thus be employed for the treatment of inflammation-induced diseases, such as arthrosis, arteriosclerosis, psoriasis, multiple sclerosis, chronic inflammatory bowel diseases (Crohn's disease, colitis ulcerosa) asthma and other allergic diseases.

The compounds of the formula I can furthermore be used for the isolation and investigation of the activity or expression of Sph kinase. In addition, they are particularly suitable for use in diagnostic methods for diseases in connection with unregulated or disturbed Sph kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit trans-plant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

WO 2007/064553 A2 describes other thiazole derivatives as CXCR3 receptor modulators.

WO 2007/020213 A2 describes other thiazolepiperidine derivatives as H3 receptor modulators.

WO 2007/019251 describes other thiazole derivatives as sphingosine kinase inhibitors. The use of the thiazole derivatives disclosed for the treatment of hyperproliferative, inflammatory and angiogenic diseases is described therein.

SUMMARY OF THE INVENTION

The invention relates to the use of compounds of the formula I

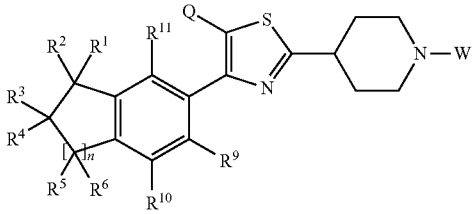

in which
R¹, R², R³,
R⁴, R⁵, R⁶ each, independently of one another, denote H or A',
Q denotes H, A, Hal, COOR⁷ or CON(R⁷R⁷'),
W denotes [C(R⁸R⁸')]$_p$Z, CO—[C(R⁸R⁸')]$_p$Z, CO—N(R⁸)—[C(R⁸R⁸')]$_p$Z, CO—O—[C(R⁸R⁸')]$_p$Z, SO₂—[C(R⁸R⁸')]$_p$Z, CO[C(R⁸R⁸')]$_p$NHCOOA or [C(R⁸R⁸')]$_p$N-HCOOA,
R⁷, R⁷' each, independently of one another, denote H or A',
R⁸, R⁸' each, independently of one another, denote H, A, OA, NAA' or Het,
R⁹ denotes H or A',
R¹⁰, R¹¹ each, independently of one another, denote H, A' or OH,
Z denotes Het, Ar or A,
A denotes unbranched or branched alkyl having 1-10 C atoms, in which 1-7 H atoms may be replaced by F, Cl, Br, OH and/or OCH₃,
and/or in which one or two non-adjacent CH₂ groups may be replaced by O, S, SO, SO₂, CO, COO, NR⁷, NR⁷CO, CONR⁷, CH=CH and/or CH≡CH groups
or
cyclic alkyl having 3-7 C atoms,
Ar denotes phenyl, naphthyl or biphenyl, each of which is unsubstituted or mono-, di-, tri-, tetra- or pentasubstituted by Hal, A, [C(R⁷R⁷')]$_p$OR⁷, [C(R⁷R⁷')]$_p$N(R⁷)₂, SR⁷, NO₂, CN, CHO, COOR⁷, CON(R⁷R⁷'), NR⁷COA, NR⁷SO₂A, SO₂N(R⁷R⁷'), S(O)$_m$A, [C(R⁷R⁷')]$_p$N(R⁷)₂, O[C(R⁷R⁷')]₂ Het, NHCOOA, NHCON(R⁷R⁷'), NHCOO[C(R⁷R⁷')]$_p$N(R⁷)₂, NHCOO[C(R⁷R⁷')]$_p$Het, NHCONH[C(R⁷R⁷')]$_p$N(R⁷)₂, NHCONH[C(R⁷R⁷')]$_p$Het, OCONH[C(R⁷R⁷')]$_p$N(R⁷)₂, OCONH[C(R⁷R⁷')]$_p$Het, CONR⁷[C(R⁷R⁷')]$_p$N(R⁷)₂, CONR⁷[C(R⁷R⁷')]$_p$Het, COA, [C(R⁷R⁷')]$_p$Het, [C(R⁷R⁷')]$_p$Ar', CO[C(R⁷R⁷')]$_p$Het, CO[C(R⁷R⁷')]$_p$Ar', CONR⁷[C(R⁷R⁷')]$_p$Ar', COO[C(R⁷R⁷')]$_p$Het, COO[C(R⁷R⁷')]$_p$Ar', S(O)$_m$[C(R⁷R⁷')]$_p$Het and/or S(O)$_m$[C(R⁷R⁷')]$_p$Ar',
Ar' denotes phenyl which is unsubstituted or mono-, di-, tri-, tetra- or pentasubstituted by Hal, A, OH, OA', NH₂, NHA, NAA', CN, CHO, COOR⁷, CON(R⁷R⁷'), NR⁷COA, NR⁷SO₂A, SO₂N(R⁷R⁷'), S(O)$_m$A and/or COA,
A' denotes unbranched or branched alkyl having 1-8 C atoms, in which 1-7 H atoms may be replaced by F, Cl and/or Br,
Het denotes a mono-, bi- or tricyclic saturated, unsaturated or aromatic heterocycle having 1 to 4 N, O and/or S atoms, which may be unsubstituted or mono-, di- or trisubstituted by Hal, A, OR⁷, [C(R⁷R⁷')]$_p$Ar, [C(R⁷R⁷')]$_p$Het', COA, CO[C(R⁷R⁷')]$_p$Ar, CO[C(R⁷R⁷')]$_p$Het', CON(R⁸)[C(R⁷R⁷')]$_p$Ar, CON(R⁸)[C(R⁷R⁷')]$_p$Het', CON(R⁷R⁷'), COOR⁷, COO[C(R⁷R⁷')]$_p$Ar, COO[C(R⁷R⁷')]$_p$Het', S(O)$_m$A, S(O)$_m$Ar, S(O)$_m$Het', NO₂, CN, NR⁷COOA, NR⁷COOAr, NR⁷COOHet', OCONHA', OCONHAr, OCONHHet', NR⁷SO₂A, NR⁷SO₂Ar, NR⁷SO₂Het', SO₂N(R⁷)A, SO₂N(R⁷)Ar, SO₂N(R⁷)Het', CHO, =S, =NH, =NA, oxy (—O⁻) and/or =O (carbonyl oxygen),
Het' denotes a monocyclic saturated heterocycle having 1 to 2 N and/or O atoms, which may be mono- or disubstituted by A, OA, OH, Hal and/or =O (carbonyl oxygen),
m denotes 0, 1 or 2,
n denotes 1, 2, or 3,
p denotes 0, 1, 2, 3 or 4,
and pharmaceutically usable salts, tautomers and stereoisomers thereof, including mixtures thereof in all ratios,
for the preparation of a medicament for the treatment of diseases which are influenced by inhibition of Sph kinase 1 by the compounds of the formula I.

The invention furthermore relates to compounds of the formula I

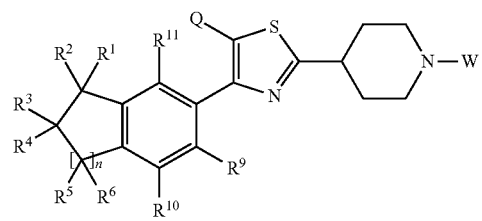

in which
R¹, R², R³,
R⁴, R⁵, R⁶ each, independently of one another, denote H or A',
Q denotes H, A, Hal, COOR⁷ or CON(R⁷R⁷'),
W denotes [C(R⁸R⁸')]$_p$Z, CO—[C(R⁸R⁸')]$_p$Z, CO—N(R⁸)—[C(R⁸R⁸')]$_p$Z,
CO—O—[C(R⁸R⁸')]$_p$Z, SO₂—[C(R⁸R⁸')]$_p$Z, CO[C(R⁸R⁸')]$_p$NHCOOA or [C(R⁸R⁸')]$_p$NHCOOA,
R⁷, R⁷' each, independently of one another, denote H or A',
R⁸, R⁸' each, independently of one another, denote H, A, OA, NAA' or Het,
R⁹ denotes H or A',
R¹⁰, R¹¹ each, independently of one another, denote H, A' or OH,
Z denotes Het, Ar or A,
A denotes unbranched or branched alkyl having 1-10 C atoms, in which 1-7 H atoms may be replaced by F, Cl, Br, OH and/or OCH₃,
and/or in which one or two non-adjacent CH₂ groups may be replaced by O, S, SO, SO₂, CO, COO, NR⁷, NR⁷CO, CONR⁷, CH=CH and/or CH≡CH groups
or
cyclic alkyl having 3-7 C atoms,
Ar denotes phenyl, naphthyl or biphenyl, each of which is unsubstituted or mono-, di-, tri-, tetra- or pentasubstituted by Hal, A, [C(R⁷R⁷')]$_p$OR⁷, [C(R⁷R⁷')]$_p$N(R⁷)₂, SR⁷, NO₂, CN, CHO, COOR⁷, CON(R⁷R⁷'), NR⁷COA, NR⁷SO₂A, SO₂N(R⁷R⁷'), S(O)$_m$A, [C(R⁷R⁷')]$_p$N(R⁷)₂, O[C(R⁷R⁷')]₂ Het, NHCOOA, NHCON(R⁷R⁷'), NHCOO[C(R⁷R⁷')]$_p$N(R⁷)₂, NHCOO[C(R⁷R⁷')]$_p$Het, NHCONH[C(R⁷R⁷')]$_p$N(R⁷)₂, NHCONH[C(R⁷R⁷')]$_p$Het, OCONH[C(R⁷R⁷')]$_p$N(R⁷)₂, OCONH[C(R⁷R⁷')]$_p$Het, CONR⁷[C(R⁷R⁷')]$_p$N(R⁷)₂, CONR⁷[C(R⁷R⁷')]$_p$Het, COA, [C(R⁷R⁷')]$_p$Het, [C(R⁷R⁷')]$_p$Ar', CO[C(R⁷R⁷')]$_p$Het, CO[C(R⁷R⁷')]$_p$Ar', CONR⁷[C(R⁷R⁷')]$_p$Ar', COO[C(R⁷R⁷')]$_p$Het, COO[C(R⁷R⁷')]$_p$Ar', S(O)$_m$[C(R⁷R⁷')]$_p$Het and/or S(O)$_m$[C(R⁷R⁷')]$_p$Ar', Ar' denotes phenyl which is unsubstituted or mono-, di-, tri-, tetra- or pentasubstituted by Hal, A, OH, OA', $NH_2$, NHA, NAA', CN, CHO, $COOR^7$, $CON(R^7R^{7'})$, $NR^7COA$, $NR^7SO_2A$, $SO_2N(R^7R^{7'})$, $S(O)_mA$ and/or COA, A' denotes unbranched or branched alkyl having 1-8 C atoms, in which 1-7 H atoms may be replaced by F, Cl and/or Br, Het denotes a mono-, bi- or tricyclic saturated, unsaturated or aromatic heterocycle having 1 to 4 N, O and/or S atoms, which may be unsubstituted or mono-, di- or trisubstituted by Hal, A, $OR^7$, $[C(R^7R^{7'})]_pAr$, $[C(R^7R^{7'})]_pHet'$, COA, $CO[C(R^7R^{7'})]_pAr$, $CO[C(R^7R^{7'})]_pHet'$, $CON(R^8)[C(R^7R^{7'})]_pAr$, $CON(R^8)[C(R^7R^{7'})]_pHet'$, $CON(R^7R^{7'})$, $COOR^7$, $COO[C(R^7R^{7'})]_pAr$, $COO[C(R^7R^{7'})]_pHet'$, $S(O)_mA$, $S(O)_mAr$, $S(O)_mHet'$, $NO_2$, CN, $NR^7COOA$, $NR^7COOAr$, $NR^7COOHet'$, OCONHA', OCONHAr, OCONHHet', $NR^7SO_2A$, $NR^7SO_2Ar$, $NR^7SO_2Het'$, $SO_2N(R^7)A$, $SO_2N(R^7)Ar$, $SO_2N(R^7)Het'$, CHO, =S, =NH, =NA, oxy (—O⁻) and/or =O (carbonyl oxygen), Het' denotes a monocyclic saturated heterocycle having 1 to 2 N and/or O atoms, which may be mono- or disubstituted by A, OA, OH, Hal and/or =O (carbonyl oxygen), m denotes 0, 1 or 2,
n denotes 1, 2 or 3,
p denotes 0, 1, 2, 3 or 4,
and pharmaceutically usable salts, tautomers and stereoisomers thereof, including mixtures thereof in all ratios;
where compounds of the formula I in which
a) W=$COCH_2$Het;
b) n=2 and W=unsubstituted alkyl having 1-10 C atoms or cycloalkyl having 3-7 C atoms,
are excluded.

The invention also relates to the precursors of the compounds of the formula I (compounds from the "C" series), to medicaments which comprise these compounds, and to the use thereof for the treatment of diseases as described for the compounds of the formula I.

Compounds of the formula I are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that
a) a compound of the formula II

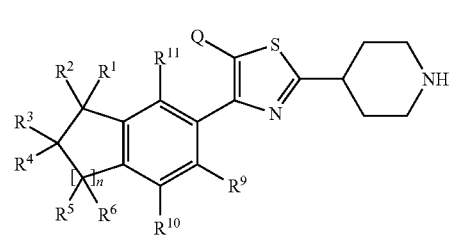

II in which $R^1$, $R^2$, $R^3$, $R^4$, $R^5$, $R^6$, $R^9$, $R^{10}$, $R^{11}$, Q and n have the meanings indicated in Claim 1,
is reacted with a compound of the formula III

L-W    III, in which W has the meaning indicated in Claim 1 and
L denotes Cl, Br, I or a free or reactively functionally modified OH group,
or
b) for the preparation of compounds of the formula I in which
W denotes $[C(R^8R^{8'})]_pZ$ or $[C(R^8R^{8'})]_pNHCOOA$,
$R^8$ denotes H,
p denotes 1, 2, 3 or 4,
$R^{8'}$, Z, A have the meanings indicated in Claim 1,
a compound of the formula II
i) is reacted with a compound of the formula IVa $R^{8'}$—CO—$[C(R^8R^{8'})]_{p-1}Z$    IVa, in which
p denotes 1, 2, 3 or 4 and
$R^{8'}$, Z have the meanings indicated in Claim 1,
in a reductive amination,
or
ii) is reacted with a compound of the formula IVb $R^{8'}$—CO—$[C(R^8R^{8'})]_{p-1}$NHCOOA    IVb, in which
p denotes 1, 2, 3 or 4 and
$R^{8'}$, A have the meanings indicated in Claim 1,
in a reductive amination,
or
b) in that they are liberated from one of their functional derivatives by treatment with a solvolysing or hydrogenolysing agent,
and/or
a base or acid of the formula I is converted into one of its salts.

Above and below, the radicals $R^1$, $R^2$, $R^3$, $R^4$, $R^5$, $R^6$, $R^9$, $R^{10}$, $R^{11}$, Q, W and n have the meanings indicated for the formula I, unless expressly stated otherwise.

The expression "carbamoyl" means "aminocarbonyl" and vice versa.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A furthermore preferably denotes unbranched or branched alkyl having 1-10 C atoms, in which 1-7 H atoms may be replaced by F, Cl, Br, OH and/or $OCH_3$, and/or in which one or two non-adjacent $CH_2$ groups may be replaced by O, $NR^7$, $SO_2$, $NR^7CO$ and/or $CONR^7$ groups.

A therefore also denotes, for example, dimethylaminoethyl, aminocarbonylmethyl, hydroxyethyl, 2,3-dihydroxypropyl, 3-hydroxypropyl, 3-methoxy-2-hydroxypropyl, N,N-diethylaminocarbonylmethyl or 2-methanesulfonyl-1-methylethyl.

Cyclic alkyl (cycloalkyl) preferably denotes cyclopropyl, cyclobutyl, cylopentyl, cyclohexyl or cycloheptyl.

A' preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

$R^1$, $R^2$ preferably denote, in each case independently of one another, H or A'.

$R^3$, $R^4$ preferably denote H.

$R^5$, $R^6$ preferably denote, in each case independently of one another, H or A'.

Q preferably denotes H.

W preferably denotes $[C(R^8R^{8'})]_pZ$, $CO-[C(R^8R^{8'})]_pZ$, $CO-N(R^8)-[C(R^8R^{8'})]_pZ$, $CO-O-[C(R^8R^{8'})]_pZ$, $CO[C(R^8R^{8'})]_pNHCOOA$ or $[C(R^8R^{8'})]_pNHCOOA$.

$R^7$, $R^{7'}$ preferably denote, in each case independently of one another, H or A'.

$R^8$, $R^{8'}$ preferably denote, in each case independently of one another, H, A or Het.

$R^9$ preferably denotes H or A', particularly preferably H.

$R^{10}$, $R^{11}$ preferably denote, in each case independently of one another, H, A' or OH, particularly preferably H.

Z preferably denotes Het or A.

Z particularly preferably denotes morpholinyl, ethylpiperidinyl, methylpyrrolidinyl, piperidinyl, pyrrolidinyl, 2,4-dioxotetrahydroquinazolinyl, 2-oxooxazolidinyl, methyl, ethyl, 4-(methoxyphenyl)piperazinyl, pyridyl, 4-(tert-butyloxycarbonyl)piperazinyl, 4-(tert-butyloxycarbonyl)morpholinyl, piperazinyl, hydroxypyrrolidinyl, N-tert-butyloxycarbonylhydroxypyrrolidinyl, dimethylaminoethyl, aminocarbonylmethyl, hydroxyethyl, 2,3-dihydroxypropyl, 3-hydroxypropyl, 3-methoxy-2-hydroxypropyl, N,N-diethylaminocarbonylmethyl or 2-methanesulfonyl-1-methylethyl, $CH(NH_2)CH_2CONH_2$ or $CH(NH_2)CH_2OH$.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p[2-(morpholin-4-yl)ethoxy] phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar very particularly preferably denotes phenyl which is unsubstituted or mono-, di-, tri-, tetra- or pentasubstituted by Hal and/or $[C(R^7R^{7'})]_pOR^7$.

Ar' preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido) phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-meth 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes a mono- or bicyclic saturated, unsaturated or aromatic heterocycle having 1 to 4 N, O and/or S atoms, which may be unsubstituted or mono-, di- or trisubstituted by A, $OR^7$, $[C(R^7R^{7'})]_pAr$, $COOR^7$ and/or $=O$ (carbonyl oxygen)

Het particularly preferably denotes pyrrolidinyl, piperidinyl, morpholinyl, oxazolidinyl, tetrahydroquinazolinyl, piperazinyl, thiazolyl, furyl, thienyl, pyrrolyl, imidazolyl, pyrazolyl, oxazolyl, isoxazolyl, isothiazolyl, pyridyl, pyrimidinyl, triazolyl, tetrazolyl, oxadiazolyl or thiadiazolyl, each of which is unsubstituted or mono-, di- or trisubstituted by A, $OR^7$, $[C(R^7R^{7'})]_pAr$, $COOR^7$ and/or $=O$ (carbonyl oxygen).

Het preferably denotes a monocyclic saturated heterocycle having 1 to 2 N and/or O atoms, which may be mono- or disubstituted by A; very particularly preferably piperidinyl, pyrrolidinyl, morpholinyl or piperazinyl, each of which which may be mono- or disubstituted by A.

Hal preferably denotes F, Cl or Br, but also I, particularly preferably F or Cl. n preferably denotes 1 or 2.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I, and the use thereof, in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia $R^1$, $R^2$ each, independently of one another, denote H or A',
$R^3$, $R^4$ denote H,
$R^5$, $R^6$ each, independently of one another, denote H or A';
in Ib Q denotes H;
in Ic W denotes $[C(R^8R^{8'})]_pZ$, $CO-[C(R^8R^{8'})]_pZ$, $CO-N(R^8)-[C(R^8R^{8'})]_pZ$, $CO-O-[C(R^8R^{8'})]_pZ$, $CO[C(R^8R^{8'})]_pNHCOOA$ or $[C(R^8R^{8'})]_pNHCOOA$;
in Id $R^7$, $R^{7'}$ each, independently of one another, denote H or A',
$R^8$, $R^{8'}$ denote H, A or Het;
in Ie Z denotes Het or A;
in If A denotes unbranched or branched alkyl having 1-10 C atoms, in which 1-7 H atoms may be replaced by F, Cl, Br, OH and/or $OCH_3$,
and/or in which one or two non-adjacent $CH_2$ groups may be replaced by O, $NR^7$, $SO_2$, $NR^7CO$ and/or $CONR^7$ groups;
in Ig Ar denotes phenyl which is unsubstituted or mono-, di-, tri-, tetra- or pentasubstituted by Hal and/or $[C(R^7R^{7'})]_pOR^7$;
in Ih Het denotes a mono- or bicyclic saturated, unsaturated or aromatic heterocycle having 1 to 4 N, O and/or S atoms, which may be unsubstituted or mono-, di- or trisubstituted by A, $OR^7$, $[C(R^7R^{7'})]_pAr$, $COOR^7$ and/or $=O$ (carbonyl oxygen);
in Ii Het denotes pyrrolidinyl, piperidinyl, morpholinyl, oxazolidinyl, tetrahydroquinazolinyl, piperazinyl, thiazolyl, furyl, thienyl, pyrrolyl, imidazolyl, pyrazolyl, oxazolyl, isoxazolyl, isothiazolyl, pyridyl, pyrimidinyl, triazolyl, tetrazolyl, oxadiazolyl or thiadiazolyl, each of which is unsubstituted or mono-, di- or trisubstituted by A, $OR^7$, $[C(R^7R^{7'})]_pAr$, $COOR^7$ and/or $=O$ (carbonyl oxygen);
in Ij $R^1$, $R^2$ each, independently of one another, denote H or A',
$R^3$, $R^4$ denote H,
$R^5$, $R^6$ each, independently of one another, denote H or A',
$R^7$, $R^{7'}$ each, independently of one another, denote H or A',
$R^8$, $R^{8'}$ each, independently of one another, denote H, A or Het,
$R^9$ denotes H or A',
$R^{10}$, $R^{11}$ each, independently of one another, denote H, A' or OH,
Q denotes H,
W denotes $[C(R^8R^{8'})]_pZ$, $CO-[C(R^8R^{8'})]_pZ$, $CO-N(R^8)-[C(R^8R^{8'})]_pZ$, $CO-O-[C(R^8R^{8'})]_pZ$, $CO[C(R^8R^{8'})]_pNHCOOA$ or $[C(R^8R^{8'})]_pNHCOOA$, Z denotes Het or A, A denotes unbranched or branched alkyl having 1-10 C atoms, in which 1-7 H atoms may be replaced by F, Cl, Br, OH and/or $OCH_3$,
and/or in which one or two non-adjacent $CH_2$ groups may be replaced by O, $NR^7$, $SO_2$, $NR^7CO$ and/or $CONR^7$ groups, A' denotes unbranched or branched alkyl having 1-8 C atoms, in which 1-7 H atoms may be replaced by F, Cl and/or Br, Ar denotes phenyl which is unsubstituted or mono-, di-, tri-, tetra- or pentasubstituted by Hal and/or $[C(R^7R^{7'})]_pOR^7$, Het denotes a mono- or bicyclic saturated, unsaturated or aromatic heterocycle having 1 to 4 N, O and/or S atoms, which may be unsubstituted or mono, di- or trisubstituted by A, $OR^7$, $[C(R^7R^{7'})]_pAr$, $COOR^7$ and/or =O (carbonyl oxygen), n denotes 1 or 2, p denotes 0, 1, 2, 3 or 4;

and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae II and III are generally known. If they are novel, however, they can be prepared by methods known per se.

Compounds of the formula I can preferably be obtained by reacting a compound of the formula II with a compound of the formula III.

In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The reaction of a compound of the formula II with a compound of the formula IVa or IVb is carried out under conditions of a reductive amination, as are known to the person skilled in the art and are described in standard works of organic chemistry.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' is an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" is a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable salts and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of sphingosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, prostate cancer, intestinal cancer, pancreatic cancer, ovarian carcinoma, renal cancer, liver carcinoma, glioblastomas and breast carcinoma.

Also encompassed is the use of the compounds according to Claim 1 according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a disease or condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use of compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

Besides the compounds of the formula I, precursors thereof (compounds from series "C") can also be used for the treatment of the said diseases.

The compounds of the formula I can be administered to patients for the treatment of cancer, in particular fast-growing tumours.

The invention thus relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to Sph kinase.

Preference is given to the use of compounds of the formula I, and pharmaceutically usable derivatives, solvates and stereoisomers thereof, including mixtures thereof in all ratios, for the preparation of a medicament for the treatment of diseases which are influenced by inhibition of SphK1 by the compounds according to Claim 1.

The diseases to be treated are preferably selected from the group hyperproliferative disease, inflammatory disease, angiogenic disease.

The hyperproliferative disease is preferably selected from the group cancer (tumour disease), atherosclerosis, restenosis, proliferative disease of the mesangial cells, psoriasis.

The tumour disease is preferably selected from the group tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma.

The proliferative disease of the mesangial cells is preferably selected from the group
glomerulonephritis, diabetic nephropathy, malignant nephrosclerosis, thrombotic microangiopathy syndrome, transplant rejection, glomerulopathy.

The inflammatory disease is preferably selected from the group Inflammatory bowel disease, arthritis, atherosclersosis, asthma, allergies, inflammatory kidney diseases, multiple sclerosis, chronic obstructive pulmonary disease, inflammatory skin diseases, pardontal diseases, psoriasis, T-cell-promoted immune disease.

The inflammatory bowel disease is preferably selected from the group ulcerative colitis, Crohn's disease, non-specific colitis.

The T-cell-promoted immune disease is preferably selected from the group allergic encephalomyelitis, allergic neuritis, transplant rejection, graft-versus-host reaction, myocarditis, thyroiditis, nephritis, systemic lupus erythematosus, insulin-dependent diabetes mellitus.

The arthritis disease is preferably selected from the group rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome.

The inflammatory kidney disease is preferably selected from the group glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease.

The inflammatory skin disease is preferably selected from the group psoriasis, atopic dermatitis, contact sensitivity, acne.

The angiogenic disease is preferably selected from the group diabetic retinopathy, arthritis, cancer, psoriasis, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome.

The disclosed compounds of the formula I can be administered in combination with other known therapeutic agents, including anticancer agents.

As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| Category | Drugs |
|---|---|
| Alkylating agents | Cyclophosphamide, Busulfan, Ifosfamide, Melphalan, Hexamethylmelamine, Thiotepa, chloroambucil, Dacarbazine, Carmustine, Lomustine, Procarbazine, Altretamine, Estramustine phosphate, Mechloroethamine, Streptozocin, Temozolomide, Semustine |
| Platinum agents | Cisplatin, Oxaliplatin, Spiroplatin, Carboxyphthalatoplatinum, Tetraplatin, Ormiplatin, Iproplatin, Carboplatin, ZD-0473 (AnorMED), Lobaplatin (Aeterna), Satraplatin (Johnson Matthey), BBR-3464 (Hoffmann-La Roche), SM-11355 (Sumitomo), AP-5280 (Access) |
| Antimetabolites | Azacytidine, Gemcitabine, Capecitabine, 5-fluorouracil, Floxuridine, 2-chlorodesoxyadenosine, 6-Mercaptopurine, 6-Thioguanine, Cytarabine, 2-fluorodesoxycytidine, Methotrexate, Idatrexate, Tomudex, Trimetrexate, Deoxycoformycin, Fludarabine, Pentostatin, Raltitrexed, Hydroxyurea, Decitabine (SuperGen), Clofarabine (Bioenvision), Irofulven (MGI Pharrna), DMDC (Hoffmann-La Roche), Ethynylcytidine (Taiho) |
| Topoisomerase inhibitors | Amsacrine, Epirubicin, Etoposide, Teniposide or mitoxantrone, Irinotecan (CPT-11), 7-ethyl-10-hydroxycamptothecin, Topotecan, Dexrazoxanet (Topo Target), Pixantrone (Novuspharrna), Rebeccamycin analogue (Exelixis), BBR-3576 (Novuspharrna), Rubitecan (SuperGen), Exatecan mesylate (Daiichi), Quinamed (ChemGenex), Gimatecan (Sigma-Tau), Diflomotecan (Beaufour-Ipsen), TAS-103 (Taiho), Elsamitrucin (Spectrum), J-107088 (Merck & Co), BNP-1350 (BioNumerik), CKD-602 (Chong Kun Dang), KW-2170 (Kyowa Hakko) |
| Antitumour antibiotics | Dactinomycin (Actinomycin D), Doxorubicin (Adriamycin), Deoxyrubicin, Valrubicin, Daunorubicin (Daunomycin), Epirubicin, Therarubicin, Idarubicin, Rubidazon, Plicamycinp, Porfiromycin, Cyanomorpholinodoxorubicin, Mitoxantron (Novantron), Amonafide, Azonafide, Anthrapyrazole, Oxantrazole, Losoxantrone, Bleomycin sulfate (Blenoxan), Bleomycinic acid, Bleomycin A, Bleomycin B, Mitomycin C, MEN-10755 (Menarini), GPX-100 (Gem Pharmaceuticals) |
| Antimitotic agents | Paclitaxel, Docetaxel, Colchicine, Vinblastine, Vincristine, Vinorelbine, Vindesine, Dolastatin 10 (NCI), Rhizoxin (Fujisawa), Mivobulin (Warner-Lambert), Cemadotin (BASF), RPR 109881A (Aventis), TXD 258 (Aventis), Epothilone B (Novartis), T 900607 (Tularik), T 138067 (Tularik), Cryptophycin 52 (Eli Lilly), Vinflunine (Fabre), Auristatin PE (Teikoku Hormone), BMS 247550 (BMS), BMS 184476 (BMS), BMS 188797 (BMS), Taxoprexin (Protarga), SB 408075 (GlaxoSmithKline), E7010 (Abbott), PG-TXL (Cell Therapeutics), IDN 5109 (Bayer), A 105972 (Abbott), A 204197 (Abbott), LU 223651 (BASF), D 24851 (ASTA Medica), ER-86526 (Eisai), Combretastatin A4 (BMS), Isohomohalichondrin-B (PharmaMar), ZD 6126 (AstraZeneca), PEG-Paclitaxel (Enzon), AZ10992 (Asahi), IDN-5109 (Indena), AVLB (Prescient NeuroPharma), Azaepothilon B (BMS), BNP-7787 (BioNumerik), CA-4-prodrug (OXiGENE), Dolastatin-10 (NrH), CA-4 (OXiGENE) |
| Aromatase inhibitors | Aminoglutethimide, Letrozole, Anastrazole, Formestan, Exemestan, Atamestan (BioMedicines), YM-511 (Yamanouchi) |
| Thymidylate synthase inhibitors | Pemetrexed (Eli Lilly), ZD-9331 (BTG), Nolatrexed (Eximias), CoFactor™ (BioKeys) |
| DNA antagonists | Trabectedin (PharmaMar), Glufosfamide (Baxter International), Albumin + 32P (Isotope Solutions), Thymectacin (NewBiotics), Edotreotid (Novartis), Mafosfamide (Baxter International), Apaziquone (Spectrum Pharmaceuticals), O6-benzylguanine (Paligent) |
| Farnesyl transferase inhibitors | Arglabin (NuOncology Labs), Ionafarnib (Schering-Plough), BAY-43-9006 (Bayer), Tipifarnib (Johnson & Johnson), Perillyl alcohol (DOR BioPharma) |
| Pump inhibitors | CBT-1 (CBA Pharma), Tariquidar (Xenova), MS-209 (Schering AG), Zosuquidar trihydrochloride (Eli Lilly), Biricodar dicitrate (Vertex) |
| Histone acetyl transferase inhibitors | Tacedinaline (Pfizer), SAHA (Aton Pharma), MS-275 (Schering AG), Pivaloyloxymethyl butyrate (Titan), Depsipeptide (Fujisawa) |
| Metalloproteinase inhibitors | Neovastat (Aeterna Laboratories), Marimastat (British Biotech), CMT-3 (CollaGenex), BMS-275291 (Celltech) |
| Ribonucleoside reductase inhibitors | Gallium maltolate (Titan), Triapin (Vion), Tezacitabine (Aventis), Didox (Molecules for Health) |
| TNF-alpha agonists/antagonists | Virulizin (Lorus Therapeutics), CDC-394 (Celgene), Revimid (Celgene) |
| Endothelin-A receptor antagonists | Atrasentan (Abbot), ZD-4054 (AstraZeneca), YM-598 (Yamanouchi) |
| Retinoic acid receptor agonists | Fenretinide (Johnson & Johnson), LGD-1550 (Ligand), Alitretinoin (Ligand) |
| Immunomodulators | Interferon, Oncophage (Antigenics), GMK (Progenics), Adenocarcinoma vaccine (Biomira), CTP-37 (AVI BioPharma), JRX-2 (Immuno-Rx), PEP-005 (Peplin Biotech), Synchrovax vaccines (CTL Immuno), Melanoma vaccine (CTL Immuno), p21-RAS vaccine (GemVax), Dexosome therapy (Anosys), Pentrix (Australian Cancer Technology), JSF-154 (Tragen), Cancer vaccine (Intercell), Norelin (Biostar), BLP-25 (Biomira), MGV (Progenics), I3-Alethin (Dovetail), CLL-Thera (Vasogen) |
| Hormonal and antihormonal agents | Oestrogens, Conjugated oestrogens, Ethynyloestradiol chlorotrianisene, Idenestrol, Hydroxyprogesterone caproate, Medroxyprogesterone, Testosterone, Testosterone propionate, Fluoxymesterone, Methyltestosterone, Diethylstilbestrol, Megestrol, Tamoxifen, Prednisone, Methylprednisolone, Prednisolone, Aminoglutethimide, Leuprolide, Goserelin, Leuporelin, Bicalutamide, Flutamide, Octreotide, Nilutamide, Mitotan, P-04 (Novogen), 2-Methoxyoestradiol |

TABLE 1-continued

| | | |
|---|---|---|
| Photodynamic agents | Toremofin<br>Dexamethasone<br>Talaporfin (Light Sciences)<br>Theralux (Theratechnologies)<br>Motexafin-Gadolinium<br>(Pharmacyclics) | (EntreMed)<br>Arzoxifen (Eli Lilly)<br>Pd-Bacteriopheophorbid<br>(Yeda)<br>Lutetium-Texaphyrin<br>(Pharmacyclics)<br>Hypericin |
| Tyrosine kinase inhibitors | Imatinib (Novartis)<br>Leflunomide (Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA)<br>SR-31747 (IL-1 antagonist, Sanofi-Synthelabo)<br>CCI-779 (mTOR kinase inhibitor, Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech)<br>CDA-II (apoptosis promoter, Everlife) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst)<br>PG2 (haematopoiesis promoter, Pharmagenesis)<br>Immunol ™ (triclosan mouthwash, Endo)<br>Triacetyluridine (uridine prodrug, Wellstat)<br>SN-4071 (sarcoma agent, Signature BioScience)<br>TransMID-107 ™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>Trans-retinic acid (differentiator, NIH)<br>MX6 (apoptosis promoter, MAXIA)<br>Apomine (apoptosis promoter, ILEX |

TABLE 1-continued

| | | |
|---|---|---|
| | SDX-101 (apoptosis promoter, Salmedix)<br>Ceflatonin (apoptosis promoter, ChemGenex) | Oncology)<br>Urocidin (apoptosis promoter, Bioniche)<br>Ro-31-7453 (apoptosis promoter, La Roche)<br>Brostallicin (apoptosis promoter, Pharmacia) |
| Alkylating agents | Cyclophosphamide<br>Busulfan<br>Ifosfamide<br>Melphalan<br>Hexamethylmelamine<br>Thiotepa<br>chloroambucil<br>Dacarbazine<br>Carmustine | Lomustine<br>Procarbazine<br>Altretamine<br>Estramustine phosphate<br>Mechloroethamine<br>Streptozocin<br>Temozolomide<br>Semustine |
| Platin agents | Cisplatin<br>Oxaliplatin<br>Spiroplatin<br>Carboxyphthalatoplatinum<br>Tetraplatin<br>Ormiplatin<br>Iproplatin | Carboplatin<br>ZD-0473 (AnorMED)<br>Lobaplatin (Aetema)<br>Satraplatin (Johnson Matthey)<br>BBR-3464 (Hoffmann-La Roche)<br>SM-11355 (Sumitomo)<br>AP-5280 (Access) |
| Anti-metabolites | Azacytidine<br>Gemcitabine<br>Capecitabine<br>5-fluorouracil<br>Floxuridine<br>2-chlorodesoxyadenosine<br>6-Mercaptopurine<br>6-Thioguanine<br>Cytarabine<br>2-fluorodesoxycytidine<br>Methotrexate<br>Idatrexate | Tomudex<br>Trimetrexate<br>Deoxycoformycin<br>Fludarabine<br>Pentostatin<br>Raltitrexed<br>Hydroxyurea<br>Decitabine (SuperGen)<br>Clofarabine (Bioenvision)<br>Irofulven (MGI Pharrna)<br>DMDC (Hoffmann-La Roche)<br>Ethynylcytidine (Taiho) |
| Topoisomerase inhibitors | Amsacrine<br>Epirubicin<br>Etoposide<br>Teniposide or mitoxantrone<br>Irinotecan (CPT-11)<br>7-ethyl-10-hydroxycamptothecin<br>Topotecan<br>Dexrazoxanet (TopoTarget)<br>Pixantrone (Novuspharrna)<br>Rebeccamycin analogue (Exelixis)<br>BBR-3576 (Novuspharrna) | Rubitecan (SuperGen)<br>Exatecan mesylate (Daiichi)<br>Quinamed (ChemGenex)<br>Gimatecan (Sigma-Tau)<br>Diflomotecan (Beaufour-Ipsen)<br>TAS-103 (Taiho)<br>Elsamitrucin (Spectrum)<br>J-107088 (Merck & Co)<br>BNP-1350 (BioNumerik)<br>CKD-602 (Chong Kun Dang)<br>KW-2170 (Kyowa Hakko) |
| Antitumour antibiotics | Dactinomycin (Actinomycin D)<br>Doxorubicin (Adriamycin)<br>Deoxyrubicin<br>Valrubicin<br>Daunorubicin (Daunomycin)<br>Epirubicin<br>Therarubicin<br>Idarubicin<br>Rubidazon<br>Plicamycinp<br>Porfiromycin<br>Cyanomorpholinodoxorubicin<br>Mitoxantron (Novantron) | Amonafide<br>Azonafide<br>Anthrapyrazole<br>Oxantrazole<br>Losoxantrone<br>Bleomycin sulfate (Blenoxan)<br>Bleomycinic acid<br>Bleomycin A<br>Bleomycin B<br>Mitomycin C<br>MEN-10755 (Menarini)<br>GPX-100 (Gem Pharmaceuticals) |
| Antimitotic agents | Paclitaxel<br>Docetaxel<br>Colchicine<br>Vinblastine<br>Vincristine<br>Vinorelbine<br>Vindesine<br>Dolastatin 10 (NCI)<br>Rhizoxin (Fujisawa)<br>Mivobulin (Warner-Lambert)<br>Cemadotin (BASF)<br>RPR 109881A (Aventis)<br>TXD 258 (Aventis)<br>Epothilone B (Novartis) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTA Medica)<br>ER-86526 (Eisai)<br>Combretastatin A4 (BMS)<br>Isohomohalichondrin-B (PharmaMar) |

TABLE 1-continued

| Category | Column 1 | Column 2 |
|---|---|---|
| | T 900607 (Tularik) | ZD 6126 (AstraZeneca) |
| | T 138067 (Tularik) | PEG-Paclitaxel (Enzon) |
| | Cryptophycin 52 (Eli Lilly) | AZ10992 (Asahi) |
| | Vinflunine (Fabre) | IDN-5109 (Indena) |
| | Auristatin PE (Teikoku Hormone) | AVLB (Prescient NeuroPharma) |
| | BMS 247550 (BMS) | Azaepothilon B (BMS) |
| | BMS 184476 (BMS) | BNP- 7787 (BioNumerik) |
| | BMS 188797 (BMS) | CA-4-prodrug (OXiGENE) |
| | Taxoprexin (Protarga) | Dolastatin-10 (NrH) |
| | | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metalloproteinase inhibitors | Neovastat (Aeterna Laboratories) | CMT -3 (CollaGenex) |
| | Marimastat | BMS-275291 (Celltech) |
| Ribonucleoside reductase inhibitors | Tezacitabine (Aventis) | |
| | (British Biotech) | Didox (Molecules for Health) |
| | Gallium maltolate (Titan) | |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | | I3-Alethin (Dovetail) |
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | Medroxyprogesterone | Leuporelin |
| | Testosterone | Bicalutamide |
| | Testosterone propionate | Flutamide |
| | Fluoxymesterone | Octreotide |
| | Methyltestosterone | Nilutamide |
| | Diethylstilbestrol | Mitotan |
| | Megestrol | P-04 (Novogen) |
| | Tamoxifen | 2-Methoxyoestradiol |
| | Toremofin | (EntreMed) |
| | Dexamethasone | Arzoxifen (Eli Lilly) |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide (Sugen/Pharmacia) | CEP- 701 (Cephalon) |
| | ZDI839 (AstraZeneca) | CEP-751 (Cephalon) |
| | Erlotinib (Oncogene Science) | MLN518 (Millenium) |
| | Canertjnib (Pfizer) | PKC412 (Novartis) |
| | Squalamine (Genaera) | Phenoxodiol O |
| | SU5416 (Pharmacia) | Trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | |
| | Tesmilifen (histamine antagonist, YM BioSciences) | Eflornithin (ODC inhibitor, ILEX Oncology) |
| | Histamine (histamine H2 receptor agonist, Maxim) | Minodronic acid (osteoclast inhibitor, Yamanouchi) |
| | Tiazofurin (IMPDH inhibitor, Ribapharm) | Indisulam (p53 stimulant, Eisai) |
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, Cell Pathways) | Immunol™ (triclosan mouthwash, Endo) |
| | AG-2037 (GART inhibitor, Pfizer) | Triacetyluridine (uridine prodrug, Wellstat) |
| | WX-UK1 (plasminogen activator inhibitor, Wilex) | SN-4071 (sarcoma agent, Signature BioScience) |
| | PBI-1402 (PMN stimulant, ProMetic LifeSciences) | TransMID-107™ (immunotoxin, KS Biomedix) |
| | Bortezomib (proteasome inhibitor, Millennium) | |
| | SRL-172 (T-cell stimulant, SR Pharma) | PCK-3145 (apoptosis promoter, Procyon) |
| | TLK-286 (glutathione-S transferase inhibitor, Telik) | Doranidazole (apoptosis promoter, Pola) |
| | PT-100 (growth factor agonist, Point Therapeutics) | CHS-828 (cytotoxic agent, Leo) |
| | Midostaurin (PKC inhibitor, Novartis) | Trans-retinic acid (differentiator, NIH) |
| | Bryostatin-1 (PKC stimulant, GPC Biotech) | MX6 (apoptosis promoter, MAXIA) |
| | CDA-II (apoptosis promoter, Everlife) | Apomine (apoptosis promoter, ILEX Oncology) |
| | SDX-101 (apoptosis promoter, | |

TABLE 1-continued

| | |
|---|---|
| Salmedix) | Urocidin (apoptosis |
| Ceflatonin (apoptosis | promoter, Bioniche) |
| promoter, ChemGenex) | Ro-31-7453 (apoptosis |
| | promoter, La Roche) |
| | Brostallicin (apoptosis |
| | promoter, Pharmacia) |

A combined treatment of this type can be achieved with the aid of simultaneous, consecutive or separate dispensing of the individual components of the treatment. Combination products of this type employ the compounds according to the invention.

Assays

The compounds of the formula I described in the examples can be tested for a kinase inhibiting activity in by the assays described below. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Tests for the Inhibition of the SphK1 Activity

Test Description

Biochemical Assay

The kinase assay is carried out as a 384-well flashplate assay.

5 nM modified SphK1, 800 nM omega-biotinyl-D-erythro-sphingosine and 1 μM ATP (with 0.3 μCi of $^{33}$P-ATP/well) are incubated in a total volume of 50 μl (25 mM HEPES, 5 mM MgCl$_2$, 1 mM dithiothreitol, 0.01% of Brij35, 0.1% of BSA (fatty acid-free), pH 7.4) without or with test substance (5-10 concentrations) at 30° C. for 120 min. The reaction is terminated using 25 μl of 200 mM EDTA solution, filtered off with suction at room temperature after 30 min, and the cavities are washed 3 times with 100 μl of 0.9% NaCl solution. The non-specific proportion of the kinase reaction (blank) is determined using 0.5 mM NaCl. Radioactivity is measured in topcount. IC$_{50}$ values are calculated using RS1.

Besides checking the activity of the substance for the purified SphK1 enzyme, it is necessary to investigate in the next step whether the substances also inhibit SphK1 in its physiological environment, i.e. in the cytoplasm of the cell.

For this purpose, the formation of S1P in U20S osteosarcoma cells which have overproduced the enzyme through the introduction of modified SphK1-cDNA is measured using two different methods:

1. The cells are incubated for 1 hour with substances and subsequently for 15 min with tritium-labelled sphingosine. The radioactively labelled sphingosine is taken up by the cells in this time and converted into S1P by SphK1. The cells are then washed and lysed using ammonia solution. In order to separate S1P from unreacted sphingosine, an extraction is carried out by addition of a chloroform/methanol mixture. Whereas the majority of the sphingosine is transferred into the organic phase, S1P accumulates in the aqueous phase and is quantified with the aid of a scintillation counter.

2. The cells are incubated for 1 hour with substances and subsequently for 15 min with sphingosine. The sphingosine is taken up by the cells in this time and converted into S1P by SphK1. The cells are then washed and lysed using methanol. The methanol solution is then evaporated, and the S1P is taken up in lipid-free serum. The quantification of the S1P is carried out using an S1P-specific antibody with the aid of a competitive ELISA assay. The biotin-linked S1P antibody is incubated with the sample solution, and this mixture is transferred into a well whose base has been coated with S1P. Only the antibodies which have not yet bound any S1P from the sample solution bind to the S1P immobilised on the plate and can be quantified, after a washing step, by addition of horseradish peroxidase-coupled streptavidin. To this end, the substrate is added to TMB, which, after conversion by the peroxidase, absorbs at a wavelength of 450 nm and can be measured. A high signal consequently corresponds to a low S1P concentration in the sample solution and a low signal correspondingly to a high S1P concentration.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, evaporated and purified by chromatography on silica gel and/or by crystallisation. Rf values on silica gel; eluent: ethyl acetate/methanol 9:1.

Mass spectrometry (MS):
EI (electron impact ionisation) M$^+$
FAB (fast atom bombardment) (M+H)$^+$
ESI (electrospray ionisation) (M+H)$^+$
APCI-MS (atmospheric pressure chemical ionisation-mass spectrometry) (M+H)$^+$.

HPLC Method:
Gradient: 4.2 min
Flow rate: 2 ml/min 99:01-0:100 water+0.1% (vol.) of TFA: acetonitrile+
0.1% (vol.) of TFA
0.0 to 0.2 min: 99:01
0.2 to 3.8 min: 99:01--->0:100
3.8 to 4.2 min: 0:100
Column: Chromolith Performance RP18e; 100 mm long, internal diameter 3 mm wavelength: 220 nm
Retention time Rt. in minutes [min].
Method B
Gradient: 4.2 min
Flow rate: 2 ml/min 99:01-0:100 water+0.1% (vol.) of formic acid: acetonitrile+0.1% (vol.) of formic acid
0.0 to 0.2 min: 99:01
0.2 to 3.8 min: 99:01--->0:100
3.8 to 4.2 min: 0:100
Column: Chromolith Performance RP18e; 100 mm long, internal diameter 3 mm wavelength: 220 nm

EXAMPLES FOR THE PREPARATION OF STARTING MATERIALS

Preparation of the Bromocarbonyl Compounds

2-Bromo-1-(5,6,7,8-tetrahydronaphthalen-2-yl)ethanone

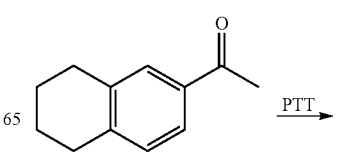

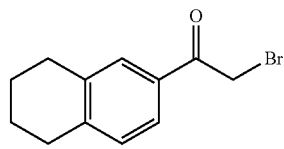

25 g (143 mmol) of 1-(5,6,7,8-tetrahydronaphthalen-2-yl)ethanone are dissolved in 750 ml of THF, 64.7 g (172 mmol) of phenyltrimethylammonium tribromide are added, and the mixture is stirred at room temperature for 15 h.

The precipitate formed is filtered, and the filtrate is evaporated to dryness. The residue is taken up in ethyl acetate, washed 2× with saturated sodium hydrogencarbonate solution and 1× with saturated sodium chloride solution, the organic phase is dried over sodium sulfate and evaporated to dryness.

Yield: 62 g, white solid; HPLC: Rt.=3.06 min.

The following compounds are prepared analogously to the procedure mentioned above. In some cases, purification by column chromatography on silica gel is necessary:

Preparation of the 2-(piperidin-4-yl)thiazole compounds

4-[4-(5,5,8,8-Tetramethyl-5,6,7,8-tetrahydronaphthalen-2-yl)thiazol-2-yl]-piperidine hydrobromide ("C1")

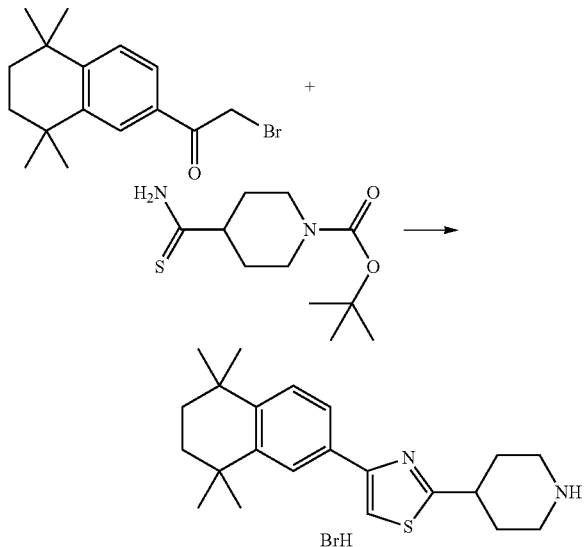

14.2 g (31.2 mmol) of 2-bromo-1-(5,5,8,8-tetramethyl-5,6,7,8-tetrahydronaphthalen-2-yl)ethanone and 7.6 g (31.2 mmol) of tert-butyl 4-thiocarbamoylpiperidine-1-carboxylate are suspended in 210 ml of ethanol and refluxed for 15 h. The reaction mixture is cooled to room temperature and evaporated. The oily residue is stirred with 50 ml of acetonitrile, the solid is filtered off with suction and washed with acetonitrile and diethyl ether. The residue is dried in vacuo.

Yield: 10.3 g, white solid. The product is in the form of the hydrobromide;

ESI: 355 (M+H); HPLC: Rt.=2.93 min.

4-[4-(5,5,8,8-Tetramethyl-5,6,7,8-tetrahydronaphthalen-2-yl)thiazol-2-yl]-piperidine hydrochloride $^1$H NMR (400 MHz, DMSO-$d_6$) δ [ppm] 9.12 (s, 1H), 8.87 (s, 1H), 7.97 (s, 1H), 7.87 (d, J=1.8, 1H), 7.66 (dd, J=1.9, 8.2, 1H), 7.38 (d, J=8.3, 1H), 3.53-3.37 (m, 3H), 3.30-3.50 (superimposed, 3H), 3.06 (q, J=11.9, 2H), 2.51 (dt, J=1.8, 3.6, 5H), 2.38-2.17 (m, 2H), 2.13-1.88 (m, 2H), 1.67 (s, 4H), 1.28 (d, J=13.7, 12H).

The following compounds are prepared analogously to the procedure mentioned above. In some cases, purification by column chromatography on silica gel or by preparative HPLC is necessary:

| Starting material | Product | Rt. in min/ HPLC-MS |
|---|---|---|
| ![sm1] | ![p1] | |
| ![sm2] | ![p2] ("C2") hydrochloride | 2.94<br>327<br>[M + H] |

$^1$H NMR (500 MHz, DMSO-$d_6$) δ [ppm] 8.99 (s, 1H), 8.73 (s, 1H), 7.98 (s, 1H), 7.91 (s, 1H), 7.68-7.57 (m, 1H), 7.09 (d, J = 8.0, 1H), 3.34-3.46 (m, 3H), 3.07 (dd, J = 9.9, 13.0, 2H), 2.74 (t, J = 6.3, 2H), 2.26 (d, J = 11.9, 2H), 1.97 (dd, J = 11.7, 22.1, 2H), 1.81-1.72 (m, 2H), 1.72-1.59 (m, 2H), 1.30 (s, 6H)

-continued
| Starting material | Product | Rt. in min/HPLC-MS |
|---|---|---|
| 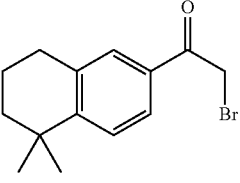 | 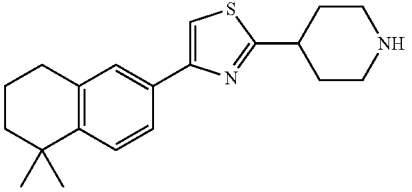  ("C3") trifluoroacetate  <sup>1</sup>H NMR (400 MHz, DMSO-d<sub>6</sub>) δ [ppm] 8.30 (s, 1H), 7.86 (s, 1H), 7.66 (d, J = 8.2, 1H), 7.59 (s, 1H), 7.39 (d, J = 8.2, 1H), 3.1-3.5 (superimposed, 4H), 2.87-2.73 (m, 4H), 2.10 (d, J = 12.7, 2H), 1.60-1.80 (m, 6H), 1.26 (s, 6H) | 2.88 327 [M + H] |
| 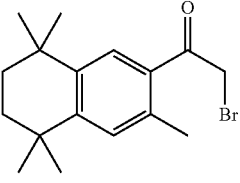 [SMILES: Cc1cc2c(cc1C(=O)CBr)C(C)(C)CCC2(C)C] | 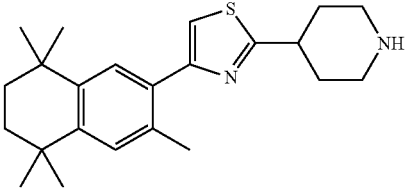  ("C4") | |
| 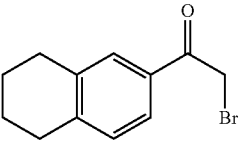 | 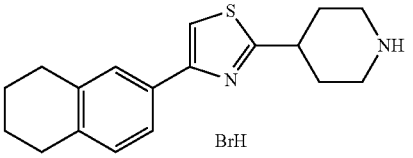 BrH  ("C5") | 2.59 299 [M + H] |
| 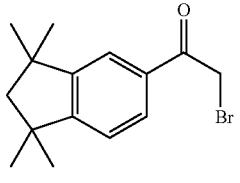 | 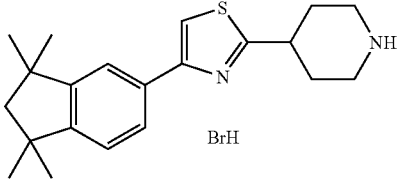 BrH  ("C6")  $^1$H NMR (400 MHz, DMSO-d$_6$) δ [ppm] 9.24 (s, 1H), 8.97 (s, 1H), 7.94 (s, 1H), 7.75 (dd, J = 1.6, 7.9, 1H), 7.69 (d, J = 1.3, 1H), 7.20 (d, J = 7.9, 1H), 3.51-3.23 (m, 3H), 3.04 (q, J = 12.4, 2H), 2.24 (d, J = 11.8, 2H), 2.07-1.81 (m, 4H), 1.30 (d, J = 9.8, 12H) | 2.98 341 [M + H] |
| 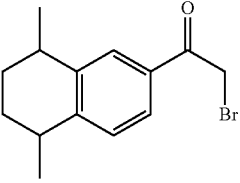 | 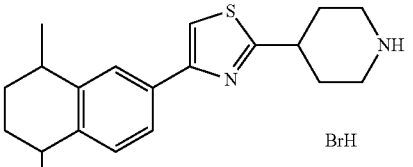 BrH  ("C7") | 2.55 (Meth. B) 327 [M + H] |

-continued
| Starting material | Product | Rt. in min/ HPLC-MS |
|---|---|---|
| 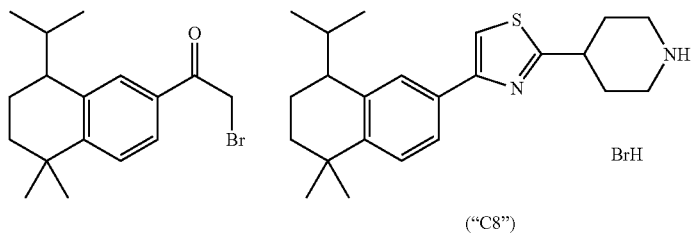 | ("C8") | |
| 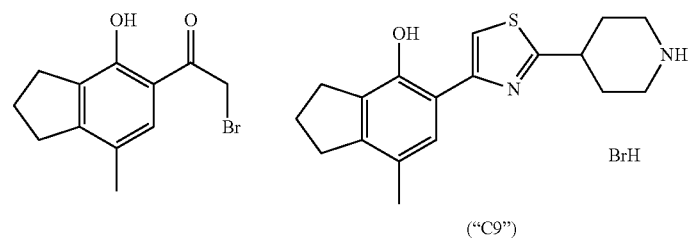 | ("C9") | |
| 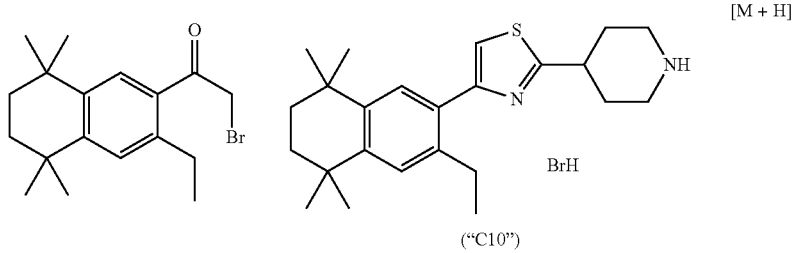 | ("C10") | 3.20<br>383<br>[M + H] |
| 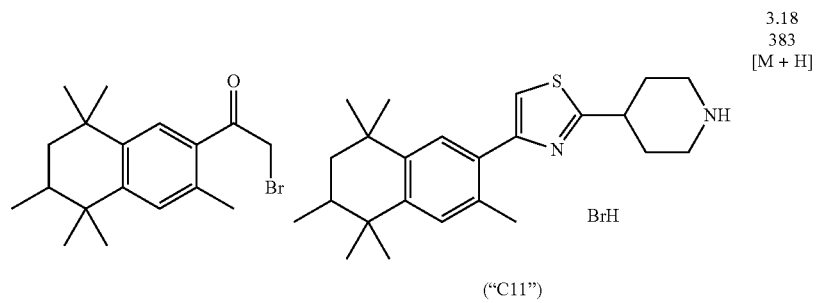 | ("C11") | 3.18<br>383<br>[M + H] |
| 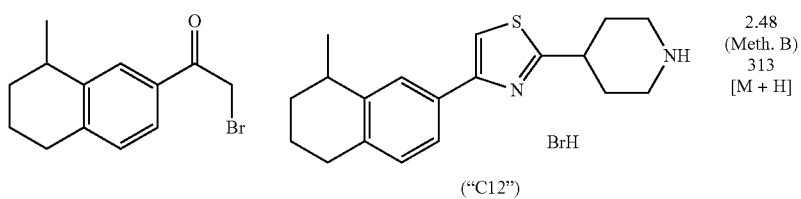 | ("C12") | 2.48<br>(Meth. B)<br>313<br>[M + H] |

Example 1

Preparation of 4-(2-methyl-3-{4-[4-(5,5,8,8-tetramethyl-5,6,7,8-tetrahydronaphthalen-2-yl)thiazol-2-yl]piperidin-1-yl}propyl)morpholine, ("A1")

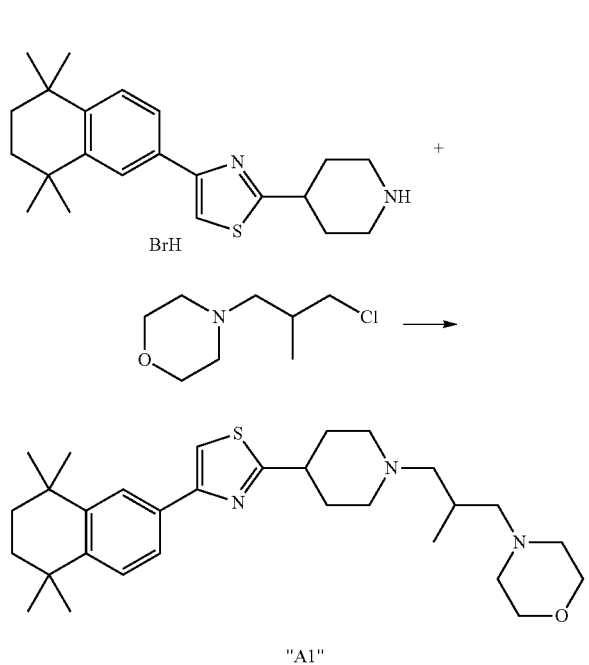

"A1"

200 mg (0.46 mmol) of 4-[4-(5,5,8,8-tetramethyl-5,6,7,8-tetrahydronaphthalen-2-yl)thiazol-2-yl]piperidine hydrobromide are irradiated in the microwave at 160° C. for 2 h with 122 mg (0.69 mmol) of 4-(3-chloro-2-methyl-propyl)morpholine in 5 ml of ethanol and 320 µl (2.3 mmol) of triethylamine. The reaction mixture is evaporated and purified by column chromatography on silica gel. The product is purified further by preparative HPLC.

Yield: 49 mg of "A1" trifluoroacetate, yellowish oil; ESI: 496 g/mol [M+H],

HPLC: Rt.=1.94 min.

Example 2

Preparation of 1'-ethyl-4-[4-(5,5,8,8-tetramethyl-5,6,7,8-tetrahydronaphthalen-2-yl)thiazol-2-yl]-[1,3]bipiperidinyl ("A2")

"A2"

500 mg (1.41 mmol) of 4-[4-(5,5,8,8-tetramethyl-5,6,7,8-tetrahydronaphthalen-2-yl)thiazol-2-yl]piperidine are suspended in 40 ml of DMF with 210 mg (1.42 mmol) of 3-chloro-1-ethylpiperidine, 360 mg (4.29 mmol) of sodium hydrogencarbonate and 210 mg (1.40 mmol) of sodium iodide and irradiated in the microwave at 120° C. for 6 h. The reaction mixture is evaporated, and the residue is dissolved in ethyl acetate and 0.1 N NaOH. The organic phase is separated off, evaporated and purified by column chromatography on silica gel.

Yield: 45 mg of "A2", hydrochloride, brown crystals, ESI: 466 g/mol [M+H];

$^1$H NMR (500 MHz, DMSO-$d_6$) δ [ppm] 11.19 (b, 1H), 7.93 (s, 1H), 7.65 (s, 2H), 7.11 (d, J=8.4, 1H), 3.0-4.0 (superimposed, 7H), 2.76 (d, J=19.6, 4H), 2.15-2.45 (b, 5H), 1.85-2.10 (m, 4H), 1.73-1.82 (m, 4H), 1.20-1.38 (m, 7H).

The following compounds are prepared analogously to the procedures mentioned above:

| Compound No. | Structure | ESI (M + H) | HPLC Rt. in min. |
|---|---|---|---|
| "A3" | 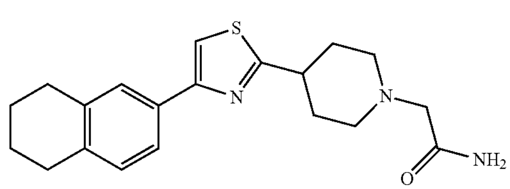 [SMILES: NC(=O)CN1CCC(c2nc(-c3ccc4c(c3)CCCC4)cs2)CC1] | 356 | |

-continued

| Compound No. | Structure | ESI (M + H) | HPLC Rt. in min. |
|---|---|---|---|
| "A4" | 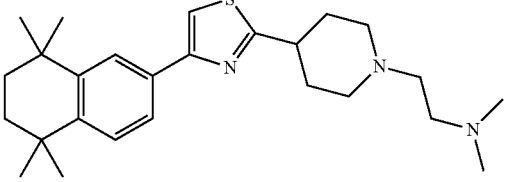<br>hydrochloride | 426 | |
| "A5" | 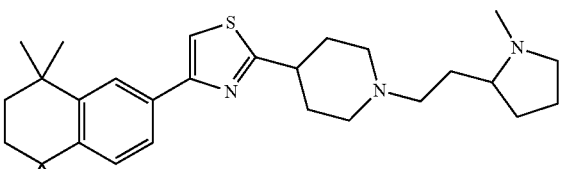<br>hydrochloride | 466 | |
| "A6" | 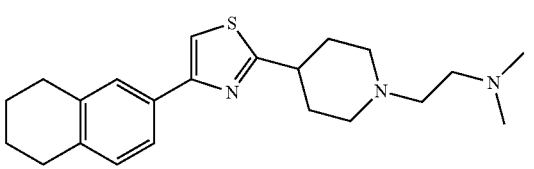<br>hydrochloride | 370 | |

$^1$H NMR (500 MHz, DMSO-d$_6$) δ [ppm] 7.86 (s, 1H), 7.60-7.66 (m, 2H), 7.10 (d, J = 8.5, 1H), 3.01-3.12 (m, 3H), 2.87-2.96 (m, 2H), 2.76 (d, J = 19.4, 4H), 2.64 (t, J = 6.3, 2H), 2.56 (s, 6H), 2.24 (t, J = 10.7, 2H), 2.08 (d, J = 11.5, 2H), 1.89-1.68 (m, 6H)

| Compound No. | Structure | ESI (M + H) | HPLC Rt. in min. |
|---|---|---|---|
| "A7" | 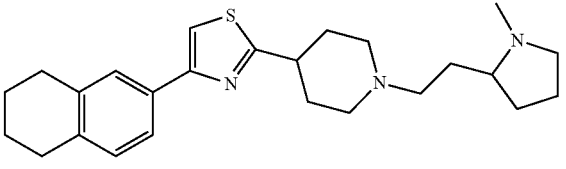<br>hydrochloride | 410 | |
| "A8" | <br>hydrochloride | 411 | |
| "A9" | 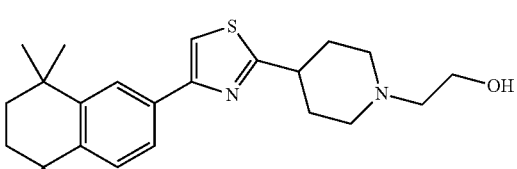<br>hydrochloride | 399 | |

$^1$H NMR (500 MHz, DMSO-d$_6$) δ 7.92 (s, 1H), 7.85 (d, J = 1.8, 1H), 7.65 (dd, J = 1.8, 8.2, 1H), 7.36 (d, J = 8.3, 1H), 5.01 (b, 1H), 3.55-3.75 (m, 2H), 3.10-3.50 (superimposed, 4H), 2.50-2.90 (m, 3H), 2.08-2.22 (m, 2H), 1.82-2.00 (m, 2H), 1.66 (s, 4H), 1.27 (d, J = 17.6, 12H)

-continued

| Compound No. | Structure | ESI (M + H) | HPLC Rt. in min. |
|---|---|---|---|
| "A10" | 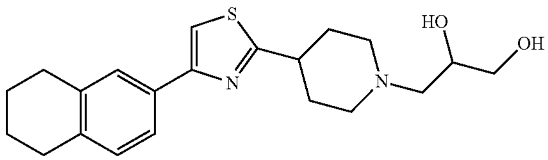 [SMILES: OCC(O)CN1CCC(c2nc(-c3ccc4c(c3)CCCC4)cs2)CC1] | 373 | |
| "A11" | hydrochloride | 343 | |
| "A12" | hydrochloride | 429 | |
| "A13" | 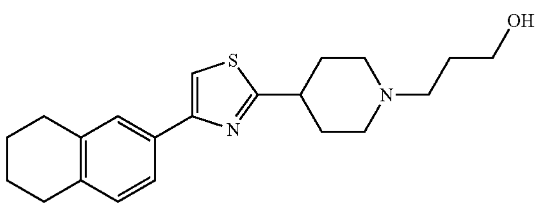 [SMILES: OCCCN1CCC(c2nc(-c3ccc4c(c3)CCCC4)cs2)CC1] | 357 | |
| "A14" | 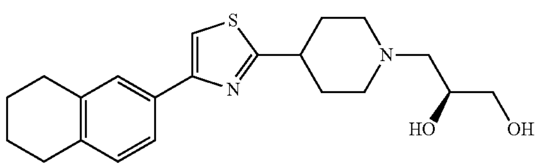 [SMILES: OC[C@@H](O)CN1CCC(c2nc(-c3ccc4c(c3)CCCC4)cs2)CC1] | 373 | |
| "A15" | 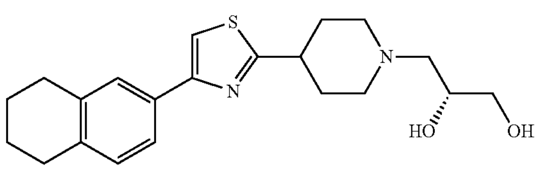 [SMILES: OC[C@H](O)CN1CCC(c2nc(-c3ccc4c(c3)CCCC4)cs2)CC1] | 373 | |
| "A16" | hydrochloride | 413 | 2.94 |

$^1$H NMR (500 MHz, DMSO-d$_6$) δ [ppm] 10.02 (s, 1H), 7.96 (s, 1H), 7.86 (s, 1H), 7.65 (d, J = 8.2, 1H), 7.37 (d, J = 8.3, 1H), 3.30-3.80 (superimposed, 5H), 3.00-3.20 (m, 4H), 2.39-2.18 (m, 3H), 2.03-2.17 (m, 2H), 1.87 (s, 2H). 1.67 (s, 4H), 1.27 (d, J = 16.8, 12H)

-continued

| Compound No. | Structure | ESI (M + H) | HPLC Rt. in min. |
|---|---|---|---|
| "A17" | hydrochloride | 443 | 3.00 |
| "A18" | hydrochloride | 468 | 2.88 |
| "A19" | hydrochloride | 466 | 2.87 |
| "A20" | hydrochloride | 470 | 2.76 |
| "A21" | hydrochloride | 452 | 2.80 |
| "A22" | trifluoroacetate | 429 | 2.88 |

| Compound No. | Structure | ESI (M + H) | HPLC Rt. in min. |
|---|---|---|---|
| "A23" | 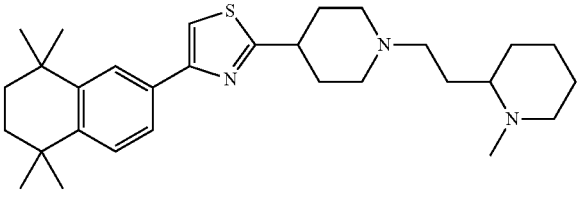<br>hydrochloride | 480 | 2.83 |
| "A24" | 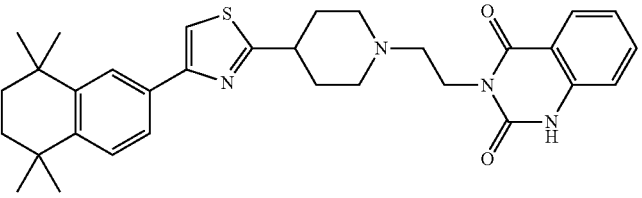<br>hydrochloride | 543 | 3.11 |
| "A25" | 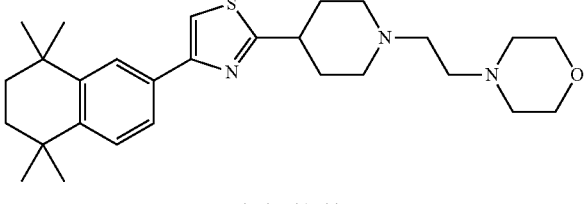<br>hydrochloride | 468 | 2.07 |
| "A26" | 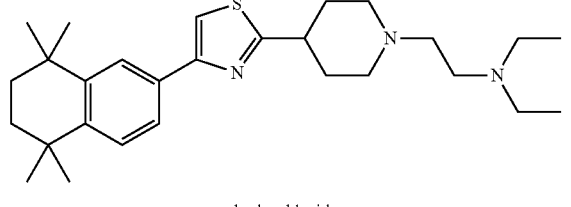<br>hydrochloride | 454 | 2.87 |
| "A27" | 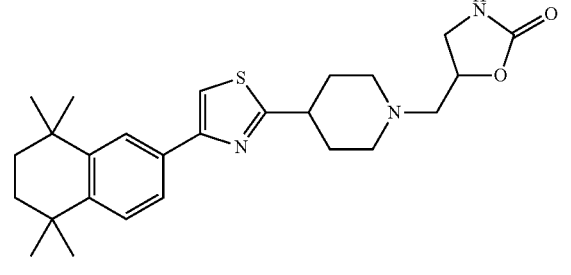 | 454 | 3.00 |
| "A28" | 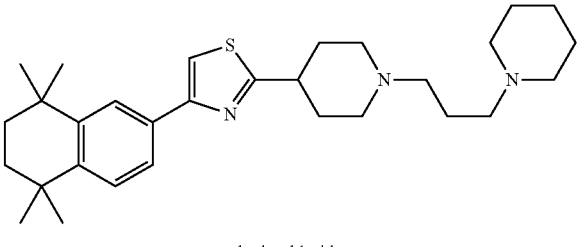<br>hydrochloride | 480 | 2.82 |

-continued

| Compound No. | Structure | ESI (M + H) | HPLC Rt. in min. |
|---|---|---|---|
| "A29" | trifluoroacetate | 440 | 2.85 |
| "A30" | hydrochloride | 496 | 2.80 |
| "A31" | hydrochloride | 482 | 3.08 |
| "A32" | 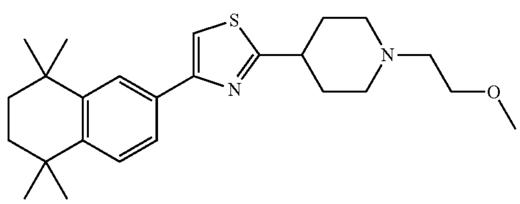 [SMILES: COCCN1CCC(c2nc(-c3ccc4c(c3)C(C)(C)CCC4(C)C)cs2)CC1] | 413 | 2.19 |

$^1$H NMR (500 MHz, DMSO-d$_6$) δ [ppm] 7.90 (s, 1H), 7.86 (d, J = 1.8, 1H), 7.65 (dd, J = 1.8, 8.2, 1H), 7.37 (d, J = 8.3, 1H), 2.80-3.60 (m, 7H), 2.50-2.70 (superimposed, 2H), 2.00-2.40 (m, 5H), 1.59-1.83 (m, 6H), 1.28 (d, J = 17.1, 12H)

| | | | |
|---|---|---|---|
| "A33" | trifluoroacetate | 369 | 3.01 |

$^1$H NMR (400 MHz, DMSO-d$_6$) δ [ppm] 10.18 (s, 1H), 7.98 (s, 1H), 7.86 (d, J = 1.7, 1H), 7.65 (d, J = 8.2, 1H), 7.37 (d, J = 8.3, 1H), 3.52 (m, 2H), 3.35 (m, 1H), 3.10 (m, 2H), 2.77 (t, J = 6.3, 3H), 2.31 (d, J = 13.9, 2H), 2.03 (d, J = 12.7, 2H), 1.66 (s, 4H), 1.27 (d, J = 13.4, 12H)

| | | | |
|---|---|---|---|
| "A34" | hydrochloride | 383 | 3.06 |

-continued

| Compound No. | Structure | ESI (M + H) | HPLC Rt. in min. |
|---|---|---|---|
| | ¹H NMR (500 MHz, DMSO-d₆) δ [ppm] 9.70 (s, 1H), 7.96 (s, 1H), 7.86 (d, J = 1.7, 1H), 7.65 (dd, J = 1.8, 8.2, 1H), 7.37 (d, J = 8.3, 1H), 3.55-3.62 (m, 2H), 3.33-3.44 (m, 1H), 3.19-2.99 (m, 4H), 2.32 (d, J = 13.9, 2H), 2.04 (d, J = 12.9, 2H), 1.67 (s, 4H), 1.35-1.18 (m, 15H) | | |
| "A35" | 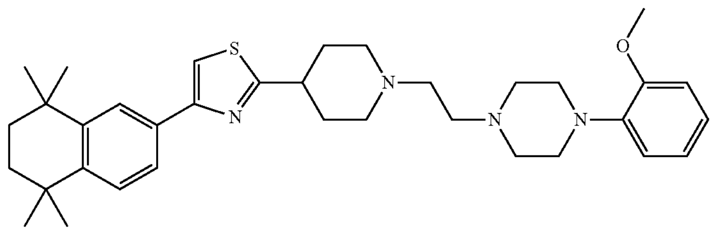 [SMILES: COc1ccccc1N1CCN(CCN2CCC(c3nc(-c4ccc5c(c4)C(C)(C)CCC5(C)C)cs3)CC2)CC1] | 573 | 2.97 |
| "A36" | 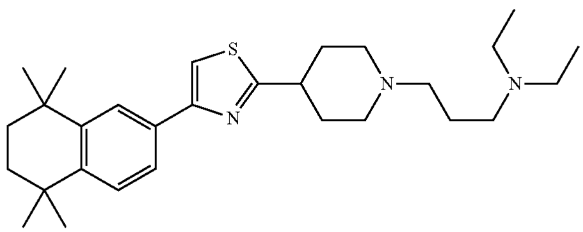 [SMILES: CCN(CC)CCCN1CCC(c2nc(-c3ccc4c(c3)C(C)(C)CCC4(C)C)cs2)CC1] | 468 | 2.80 |
| "B1" | 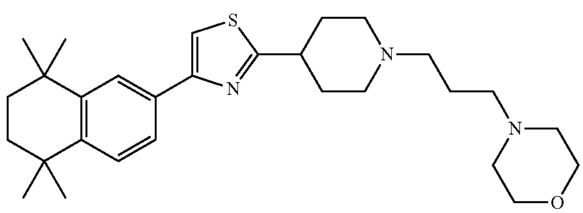 [SMILES: CC1(C)CCC(C)(C)c2cc(-c3csc(C4CCN(CCCN5CCOCC5)CC4)n3)ccc21] | 482 (M + H) | 3.03 |
| "B2" | 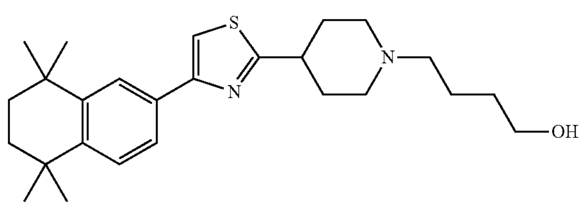 | 427 (M + H) | 2.77 (Meth. B) |
| | trifluoroacetate | | |
| | ¹H NMR (400 MHz, DMSO-d₆) δ [ppm] 8.14 (s, 1H), 7.89 (s, 1H), 7.84 (d, J = 1.8, 1H), 7.64 (dd, J = 1.8, 8.2, 1H), 7.35 (d, J = 8.2, 1H), 4.06 (b, 1H), 3.40 (t, J = 6.2, 2H), 3.04 (m, 1H), 2.98 (d, J = 11.6, 2H), 2.35 (t, J = 6.9, 2H), 2.10 (dd, J = 13.4, 26.1, 4H), 1.73 (dd, J = 12.1, 24.1, 2H), 1.66 (s, 4H), 1.56-1.39 (m, 4H), 1.27 (d, J = 17.2, 12H) | | |
| "B3" | 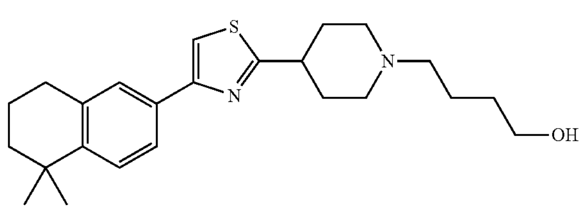 [SMILES: CC1(C)CCCc2cc(-c3csc(C4CCN(CCCCO)CC4)n3)ccc21] | 399 (M + H) | 2.89 |
| | ¹H NMR (400 MHz, DMSO-d₆) δ [ppm] 7.8 (s, 1H), 7.65 (d, J = 8.2, 1H), 7.59 (s, 1H), 7.38 (d, J = 8.2, 1H), 4.52 (b, 1H), 3.40 (t, J = 6.0, 2H), 2.99 (dt, J = 6.0, 7.8, 1H), 2.93 (d, J = 11.8, 2H), 2.76 (t, J = 6.3, 2H), 2.30 (t, J = 6.9, 2H), 2.03 (t, J = 10.8, 4H), 1.81-1.58 (m, 6H), 1.54-1.38 (m, 4H), 1.25 (s, 6H) | | |

-continued

| Compound No. | Structure | ESI (M + H) | HPLC Rt. in min. |
|---|---|---|---|
| "B4" | hydrochloride | 399 (M + H) | 3.05 |
| "B5" | hydrochloride | 427 (M + H) | 3.09 |
| "B6" | hydrochloride | 413 (M + H) | 3.13 |

Example 3

Preparation of tert-butyl (2-{4-[4-(5,5,8,8-tetramethyl-5,6,7,8-tetrahydronaphthalen-2-yl)thiazol-2-yl]piperidin-1-yl}ethyl)carbamate ("A37")

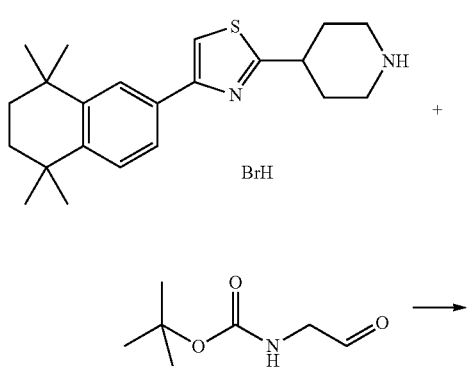

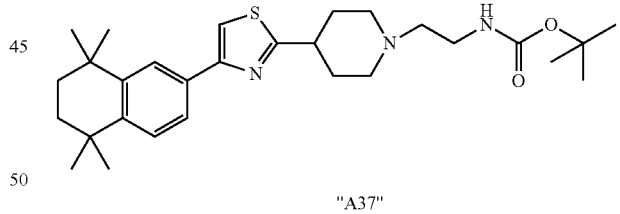

"A37"

10 ml of THF and 200 μl of glacial acetic acid are added to 200 mg (0.46 mmol) of 4-[4-(5,5,8,8-tetramethyl-5,6,7,8-tetrahydronaphthalen-2-yl)thiazol-2-yl]piperidine hydrobromide, and 154 mg (0.92 mmol) of tert-butyl (2-oxoethyl) carbamate are added. 195 mg (0.92 mmol) of sodium trisacetoxyborohydride are subsequently added, and the reaction mixture is stirred at room temperature for 24 h. The reaction mixture is filtered, the mother liquor is evaporated, and the residue is purified by preparative HPLC, giving "A37";

ESI: 498 (M+H), HPLC: 3.34 min.

The following compounds are prepared analogously to the procedure mentioned above:

| Compound No. | Structure | ESI (M+H) | HPLC Rt. in min. |
|---|---|---|---|
| "A38" | 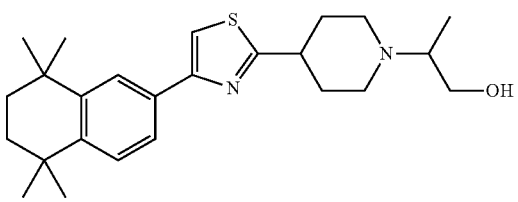 [SMILES: CC(CO)N1CCC(c2nc(-c3ccc4c(c3)C(C)(C)CCC4(C)C)cs2)CC1] | 413 | 3.05 |
| "A39" | 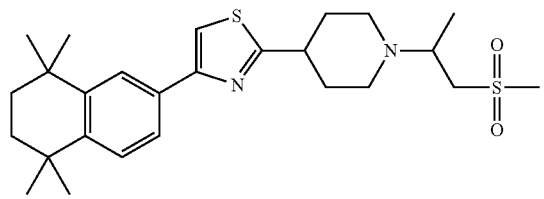 [SMILES: CC(CS(C)(=O)=O)N1CCC(c2nc(-c3ccc4c(c3)C(C)(C)CCC4(C)C)cs2)CC1] | 474 | 3.71 |
| "A40" | 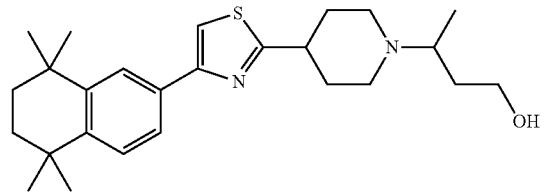 [SMILES: CC(CCO)N1CCC(c2nc(-c3ccc4c(c3)C(C)(C)CCC4(C)C)cs2)CC1] | 427 | 3.04 |
$^1$H NMR (400 MHz, DMSO-d$_6$) δ [ppm] 7.93 (s, 1H), 7.86 (d, J = 1.8, 1H), 7.66 (dd, J = 1.8, 8.2, 1H), 7.37 (d, J = 8.3, 1H), 2.80-3.60 (m, 10H), 1.7-2.3 (m, 6H), 1.67 (b, 4H), 1.3-1.66 (m, 2H), 1.28 (d, J = 13.5, 12H)
| | | | |
|---|---|---|---|
| "A71" | 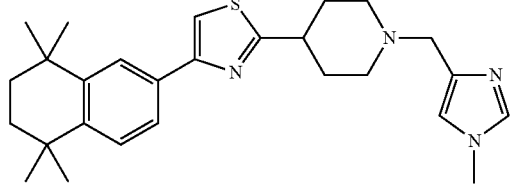 | 449 | 2.78 |
| "A72" | 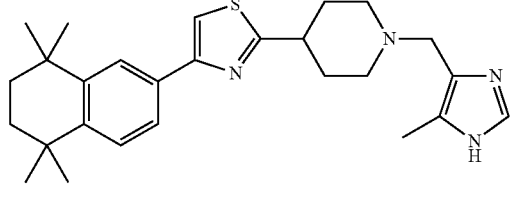 [SMILES: Cn1cnc(CN2CCC(c3nc(-c4ccc5c(c4)C(C)(C)CCC5(C)C)cs3)CC2)c1] | 449 | 2.84 |
trifluoroacetate
$^1$H NMR (500 MHz, DMSO-d$_6$) δ [ppm] 15.53-12.89 (m, 1H), 10.87-9.73 (m, 1H), 8.93 (s, 1H), 7.96 (s, 1H), 7.85 (d, J = 1.8, 1H), 7.63 (dd, J = 1.8, 8.2, 1H), 7.37 (d, J = 8.3, 1H), 4.46 (s, 2H), 3.78-2.94 (m, 5H), 2.43-2.21 (m, 5H), 1.96 (m, 2H), 1.66 (s, 4H), 1.27 (d, J = 14.0, 12H)
| | | | |
|---|---|---|---|
| "A73" | 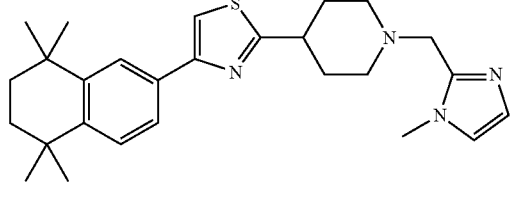 | 449 | 2.98 |

| Compound No. | Structure | ESI (M + H) | HPLC Rt. in min. |
|---|---|---|---|
| "A74" | 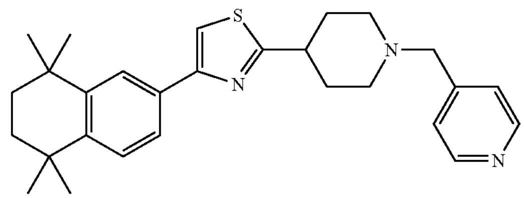 [SMILES: CC1(C)CCC(C)(C)c2cc(-c3csc(C4CCN(Cc5ccncc5)CC4)n3)ccc21] | 446 | 2.83 |
| "A75" | | 435 | 2.78 | trifluoroacetate

¹H NMR (500 MHz, DMSO-d₆) δ [ppm] 9.22 (s, 1 H), 7.80-8.00 (m, 3H), 7.63 (d, J = 8.2, 1H), 7.36 (d, J = 8.1, 1H), 4.53 (s, 2H), 3.59 (b, 2H), 3.47-3.34 (m, 1H), 3.18 (b, 2H), 2.32 (m, 2H), 2.10-1.90 (m, 2H), 1.66 (s, 4H), 1.26 (d, J = 15.6, 12H)

| | | | |
|---|---|---|---|
| "A76" | | 468 | 2.78 |
| "A77" | | 446 | 3.19 |
| "B7" | | 435 (M + H) | 3.08 | trifluoroacetate

¹H NMR (400 MHz, DMSO-d₆) δ [ppm] 9.73 (s, 1H), 7.95 (s, 1H), 7.85 (m, 2H), 7.63 (d, J = 8.2, 1 H), 7.36 (d, J = 8.3, 1H), 6.46 (d, J = 2.1, 1H), 4.36 (s, 2H), 3.56 (d, J = 12.1, 2H), 3.20-3.40 (m, 2H), 3.14 (d, J = 10.6, 2H), 2.41-2.18 (m, 3H), 2.06-1.89 (m, 2H), 1.66 (s, 4H), 1.27 (d, J = 15.1, 12H).

| | | | |
|---|---|---|---|
| "B8" | | 448 (M + H) | 3.29 | trifluoroacetate

-continued

| Compound No. | Structure | ESI (M + H) | HPLC Rt. in min. |
|---|---|---|---|
| "B9" | trifluoroacetate | 465 (M + H) | 3.09 |
| "B10" | trifluoroacetate | 441 (M + H) | 3.07 |

¹H NMR (400MHz, DMSO-d₆) δ [ppm] 9.06 (s, 1H), 7.96 (s, 1H), 7.86 (d, J = 1.8, 1H), 7.64 (dd, J = 1.8, 8.2, 1H), 7.37 (d, J = 8.3, 1H), 4.42 (b, 1H), 3.62 (d, J = 11.0, 2H), 3.41 (superimposed, 2H), 3.15-3.02 (m, 4H), 2.20-2.40 (m, 3H), 1.98 (q, J = 12.6, 2H), 1.67 (m, 6H), 1.47 (m, 2H), 1.35 (m, 2H), 1.27 (d, J = 16.1, 12H)

| Compound No. | Structure | ESI (M + H) | HPLC Rt. in min. |
|---|---|---|---|
| "B11" | trifluoroacetate | 463 (M + H) | 3.15 |
| "B12" | trifluoroacetate | 464 (M + H) | 3.20 |
| "B13" | hydrochloride | 435 (M + H) | 3.05 |

¹H NMR (400 MHz, DMSO-d₆) δ [ppm] 7.98 (s, 1H), 7.85 (s, 1H), 7.72 (s, 2H), 7.64 (d, J = 10.0, 1H), 7.37 (d, J = 8.3, 1H), 4.49 (b, 2H), 3.0-4.0 (superimposed, 8H), 2.33 (s, 2H), 2.19-2.00 (m, 2H), 1.66 (s, 4H), 1.27 (d, J = 12.3, 12H)

-continued

| Compound No. | Structure | ESI (M + H) | HPLC Rt. in min. |
|---|---|---|---|
| "B14" | 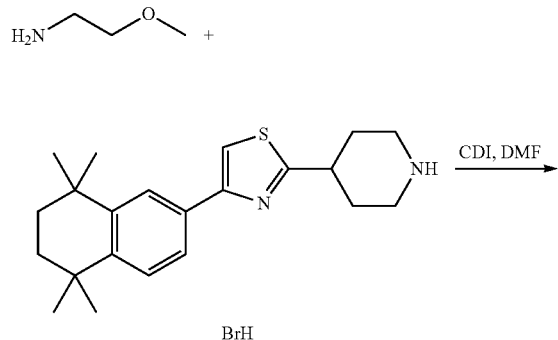 trifluoroacetate | 477 (M + H) | 3.38 |

Example 4

Preparation of tert-butyl (2-{4-[4-(5,5,8,8-tetramethyl-5,6,7,8-tetrahydronaphthalen-2-yl)thiazol-2-yl]piperidin-1-yl}ethyl)carbamate ("A41")

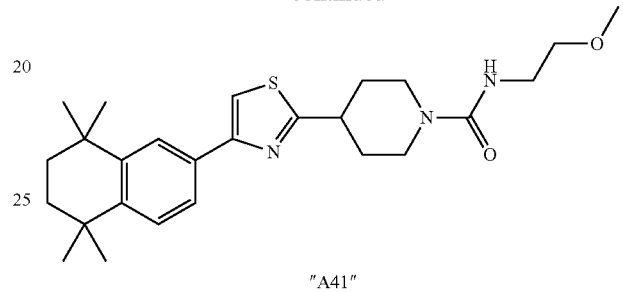

"A41"

30 µl (0.35 mmol) of 2-methoxyethylamine are dissolved in 3 ml of DMF, 56 mg (0.35 mmol) of 1,1'-carbonyldiimidazole are added, and the mixture is stirred at room temperature for 2 h. 100 mg (0.23 mmol) of 4-[4-(5,5,8,8-tetramethyl-5,6,7,8-tetrahydronaphthalen-2-yl)thiazol-2-yl]-piperidine hydrobromide and 64 µl (0.46 mmol) of triethylamine are subsequently added, and the reaction mixture is stirred at room temperature for 15 h. The reaction mixture is evaporated, and the residue is purified by column chromatography on silica gel.

Yield: 13 mg of "A41", white solid; ESI: 456 (M+H), HPLC: 3.71 min.

The following compounds are prepared analogously to the procedure mentioned above:

| Compound No. | Structure | ESI (M + H) | HPLC Rt. in min. |
|---|---|---|---|
| "A42" | 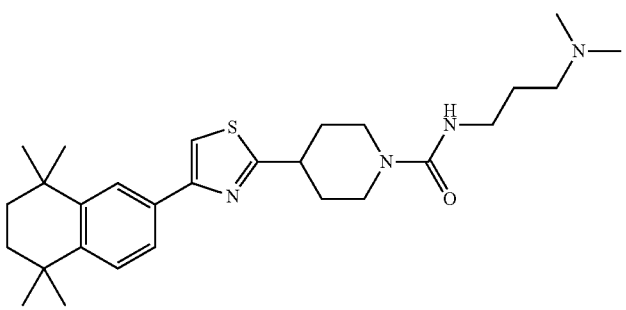 [SMILES: CN(C)CCCNC(=O)N1CCC(c2nc(-c3ccc4c(c3)C(C)(C)CCC4(C)C)cs2)CC1] | 484 | 3.16 |

-continued

| Compound No. | Structure | ESI (M + H) | HPLC Rt. in min. |
| --- | --- | --- | --- |
| "A43" | 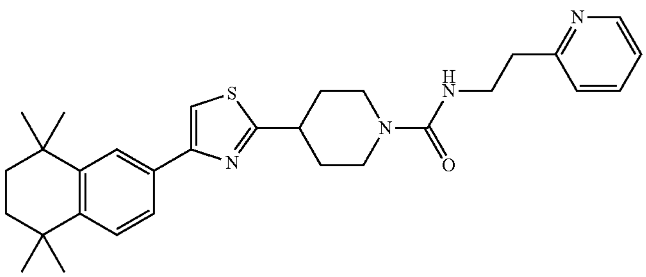 [SMILES: CC1(C)CCC(C)(C)c2cc(-c3csc(C4CCN(C(=O)NCCc5ccccn5)CC4)n3)ccc21] | 504 | 3.17 |
| "A44" | 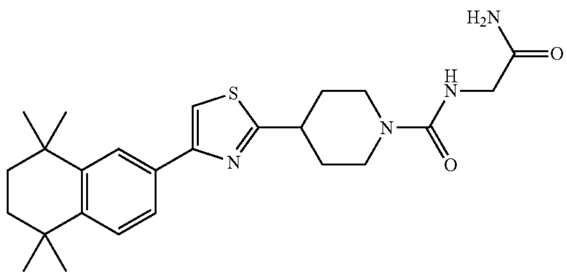 [SMILES: CC1(C)CCC(C)(C)c2cc(-c3csc(C4CCN(C(=O)NCC(N)=O)CC4)n3)ccc21] | 456 | 3.33 |
| "A45" | 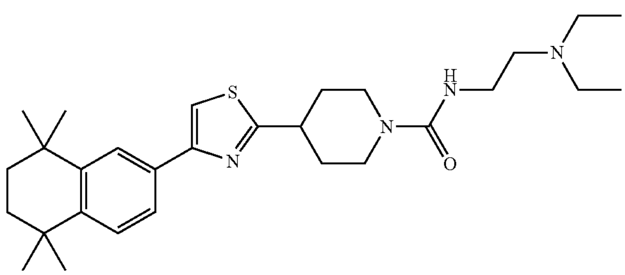 [SMILES: CCN(CC)CCNC(=O)N1CCC(c2nc(-c3ccc4c(c3)C(C)(C)CCC4(C)C)cs2)CC1] | 498 | 3.26 |
| "A78" | 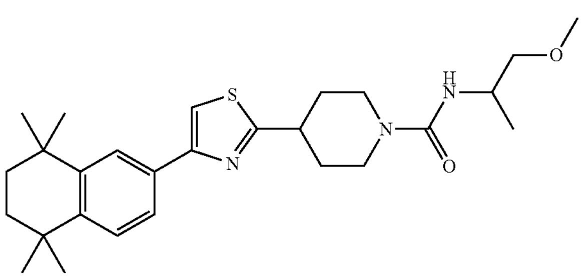 [SMILES: COCC(C)NC(=O)N1CCC(c2nc(-c3ccc4c(c3)C(C)(C)CCC4(C)C)cs2)CC1] | 470 | 3.76 |
| "A79" | 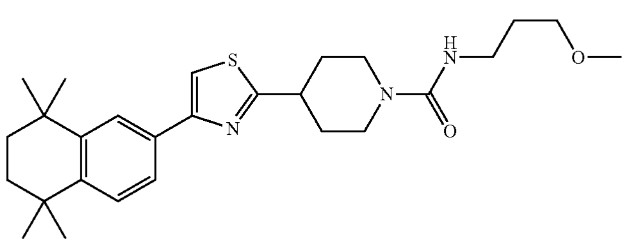 [SMILES: COCCCNC(=O)N1CCC(c2nc(-c3ccc4c(c3)C(C)(C)CCC4(C)C)cs2)CC1] | 470 | 3.74 |

Example 5

Preparation of 3-methoxypropyl 4-[4-(5,5,8,8-tetramethyl-5,6,7,8-tetrahydronaphthalen-2-yl)thiazol-2-yl]piperidine-1-carboxylate ("A46")

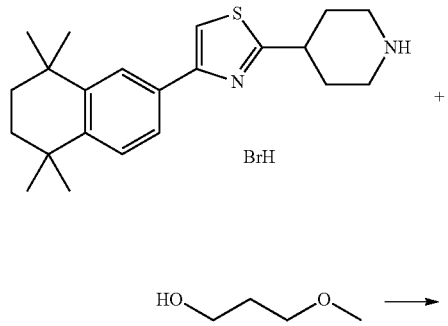

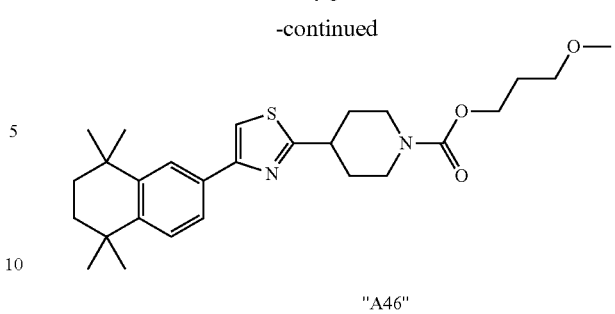

"A46"

41 µl (0.42 mmol) of 3-methoxy-1-propanol are dissolved in 3 ml of DMF, 69 mg (0.42 mmol) of 1,1'-carbonyldiimidazole are added, and the mixture is stirred at room temperature for 2 h. 122 mg (0.28 mmol) of 4-[4-(5,5,8,8-tetramethyl-5,6,7,8-tetrahydronaphthalen-2-yl)thiazol-2-yl]-piperidine hydrobromide are subsequently added, and the reaction mixture is stirred at room temperature for 3 days. The reaction mixture is evaporated, the residue is taken up in ethyl acetate and washed with 1 N HCl, saturated sodium hydrogencarbonate solution and saturated sodium chloride solution. The crude mixture is purified by column chromatography on silica gel. Yield: 90 mg of "A46", ESI: 471 (M+H), HPLC: 4.20 min.

The following compounds are prepared analogously to the procedure mentioned above:

| Compound No. | Structure | ESI (M + H) | HPLC Rt. in min. |
|---|---|---|---|
| "A47" | trifluoroacetate | 514 | 3.27 |
| "A48" | 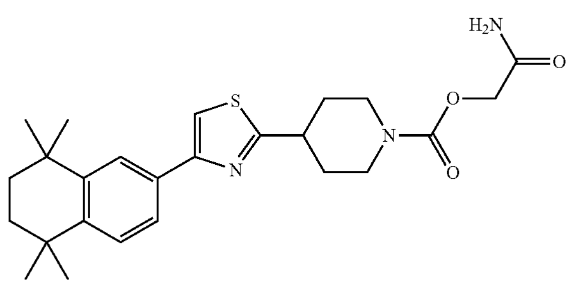 [SMILES: CC1(C)CCC(C)(C)c2cc(-c3csc(C4CCN(C(=O)OCC(N)=O)CC4)n3)ccc21] | 504 | 3.17 |
| "A49" | 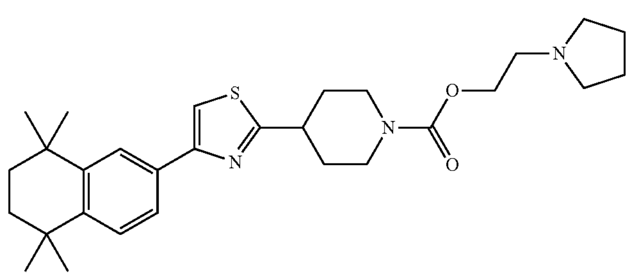 [SMILES: CC1(C)CCC(C)(C)c2cc(-c3csc(C4CCN(C(=O)OCCN5CCCC5)CC4)n3)ccc21] | 496 | 3.28 |

-continued

| Compound No. | Structure | ESI (M + H) | HPLC Rt. in min. |
|---|---|---|---|
| "A50" | 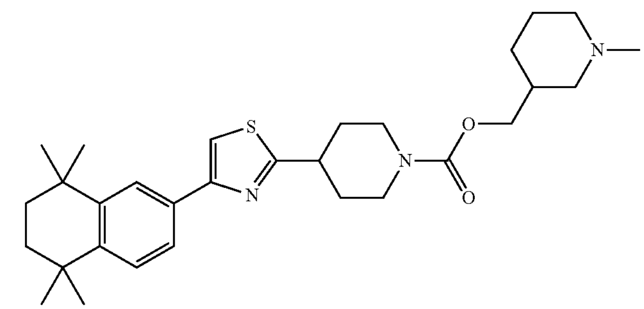 | 510 | 3.32 |
| "B15" | trifluoroacetate | 598 (M + H) | 4.25 |

Example 6

Preparation of 2-pyridin-4-yl-1-{4-[4-(5,5,8,8-tetramethyl-5,6,7,8-tetrahydronaphthalen-2-yl)thiazol-2-yl]piperidin-1-yl}ethanone ("A51")

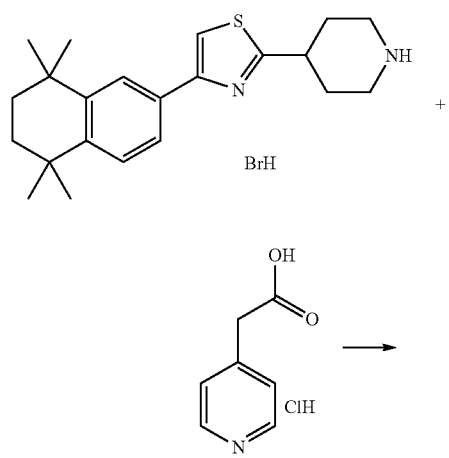

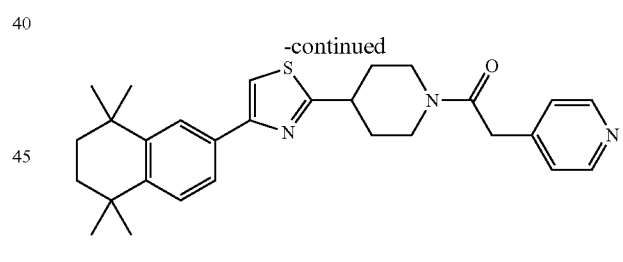

"A51"

200 mg (0.46 mmol) of 4-[4-(5,5,8,8-tetramethyl-5,6,7,8-tetrahydronaphthalen-2-yl)thiazol-2-yl]piperidine hydrobromide, 81 mg (0.46 mmol) of pyridin-4-ylacetic acid, 202 µl (1.84 mmol) of 4-methylmorpholine, 361 mg (1.84 mmol) of EDCl and 135 mg (0.73 mmol) of HOBt are dissolved in 10 ml of THF and stirred at room temperature for 24 h. The reaction mixture is added to saturated ammonium chloride solution and extracted with ethyl acetate. The organic phase is separated off, dried over sodium sulfate and evaporated to dryness. The crude mixture is purified by column chromatography on silica gel.

Yield: 70 mg of "A51", ESI: 474 (M+H), HPLC: 3.18 min.

The following compounds are prepared analogously to the procedure mentioned above:

| Compound No. | Structure | ESI (M + H) | HPLC Rt. in min. |
|---|---|---|---|
| "A52" | 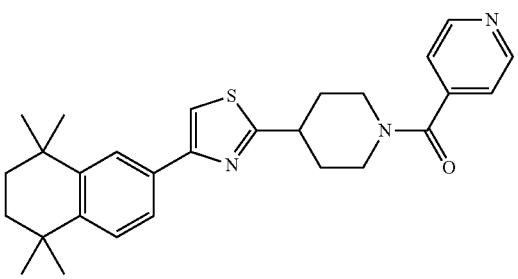 [SMILES: CC1(C)CCC(C)(C)c2cc(-c3csc(C4CCN(C(=O)c5ccncc5)CC4)n3)ccc21] | 460 | 3.24 |
| "A53" | 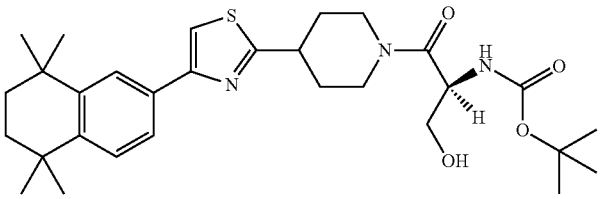 [SMILES: CC(C)(C)OC(=O)N[C@@H](CO)C(=O)N1CCC(c2nc(-c3ccc4c(c3)C(C)(C)CCC4(C)C)cs2)CC1] | 542 | |
| "A54" | 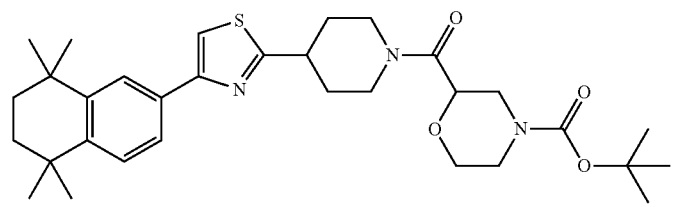 [SMILES: CC(C)(C)OC(=O)N1CCOC(C(=O)N2CCC(c3nc(-c4ccc5c(c4)C(C)(C)CCC5(C)C)cs3)CC2)C1] | 568 | |
| "A55" | 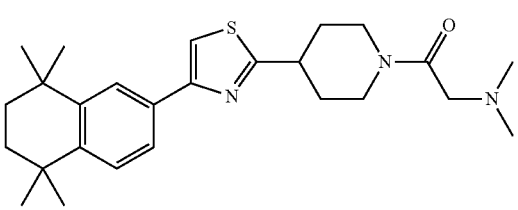 hydrochloride | 440 | |
| "A56" | 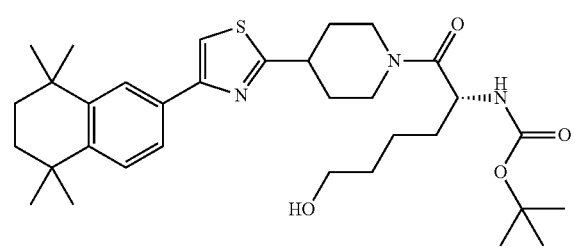 [SMILES: CC(C)(C)OC(=O)N[C@H](CCCCO)C(=O)N1CCC(c2nc(-c3ccc4c(c3)C(C)(C)CCC4(C)C)cs2)CC1] | 584 | |
| "A57" | 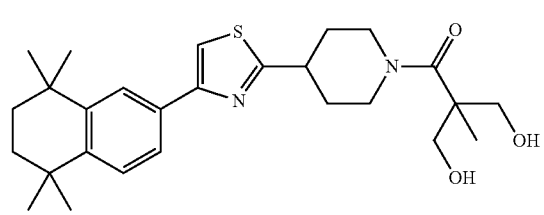 [SMILES: CC(CO)(CO)C(=O)N1CCC(c2nc(-c3ccc4c(c3)C(C)(C)CCC4(C)C)cs2)CC1] | 471 | |

-continued

| Compound No. | Structure | ESI (M + H) | HPLC Rt. in min. |
|---|---|---|---|
| "A58" | 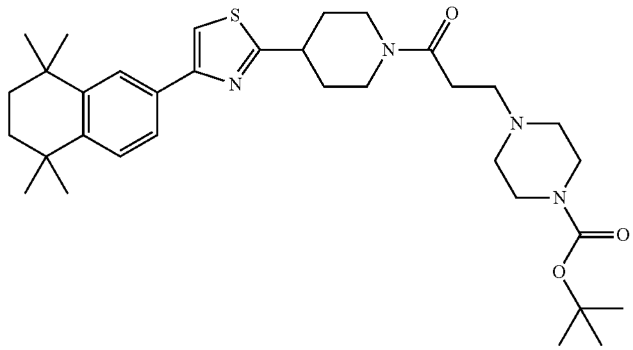 [SMILES: CC(C)(C)OC(=O)N1CCN(CCC(=O)N2CCC(c3nc(-c4ccc5c(c4)C(C)(C)CCC5(C)C)cs3)CC2)CC1] | 595 | |
| "A59" | 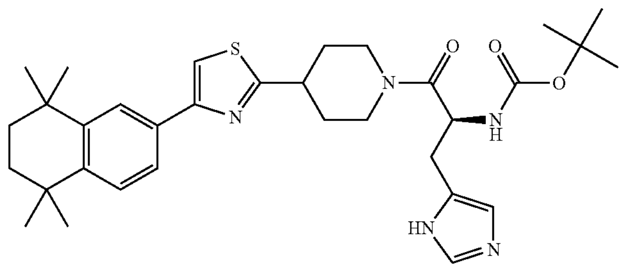 [SMILES: CC(C)(C)OC(=O)N[C@@H](Cc1cnc[nH]1)C(=O)N1CCC(c2nc(-c3ccc4c(c3)C(C)(C)CCC4(C)C)cs2)CC1] | 592 | |
| "A60" | 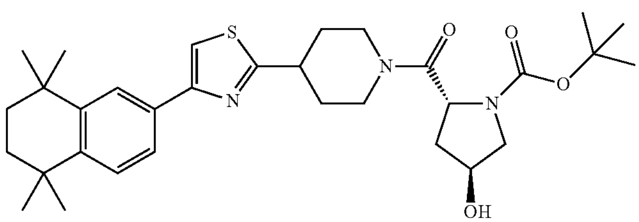 [SMILES: CC(C)(C)OC(=O)N1C[C@@H](O)C[C@@H]1C(=O)N1CCC(c2nc(-c3ccc4c(c3)C(C)(C)CCC4(C)C)cs2)CC1] | 568 | |
| "A61" | 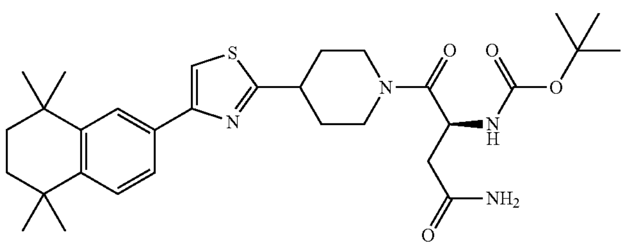 [SMILES: CC(C)(C)OC(=O)N[C@@H](CC(N)=O)C(=O)N1CCC(c2nc(-c3ccc4c(c3)C(C)(C)CCC4(C)C)cs2)CC1] | 569 | |
| "A62" | 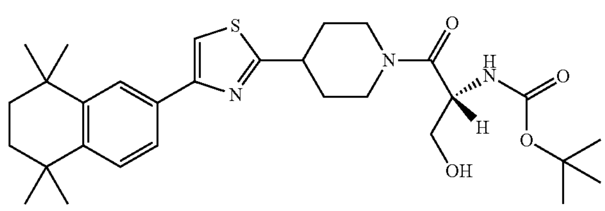 [SMILES: CC(C)(C)OC(=O)N[C@H](CO)C(=O)N1CCC(c2nc(-c3ccc4c(c3)C(C)(C)CCC4(C)C)cs2)CC1] | 542 | |
| "A80" | 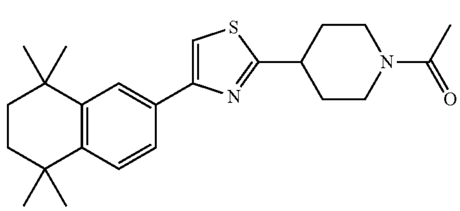 [SMILES: CC(=O)N1CCC(c2nc(-c3ccc4c(c3)C(C)(C)CCC4(C)C)cs2)CC1] | 397 | 3.71 |

Example 7

Preparation of (S)-2-amino-3-(3H-imidazol-4-yl)-1-{4-[4-(5,5,8,8-tetramethyl-5,6,7,8-tetrahydronaphthalen-2-yl)thiazol-2-yl]piperidin-1-yl}-propan-1-one ("A63")

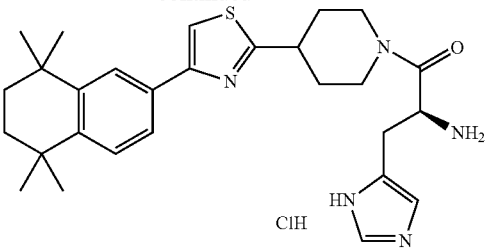

"A63"

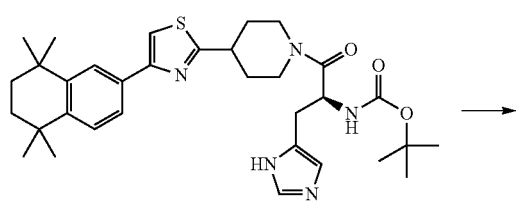

250 mg (0.42 mmol) of tert-butyl ((S)-1-(3H-imidazol-4-ylmethyl)-2-oxo-2-{4-[4-(5,5,8,8-tetramethyl-5,6,7,8-tetrahydronaphthalen-2-yl)thiazol-2-yl]-piperidin-1-yl}ethyl)carbamate are dissolved in 20 ml of dichloromethane and 1 ml of trifluoroacetic acid and stirred at room temperature for 12 h. The reaction mixture is washed with 0.1 N NaOH, the organic phase is dried over sodium sulfate and purified by column chromatography on silica gel. The crude product is dissolved in acetone, and a pH of 4 is set using 1 N HCl. A white precipitate forms in the process, which is filtered off with suction, washed with ether and dried in vacuo. Yield: 200 mg of "A63" hydrochloride, white solid; ESI: 492 (M+H).

The following compounds are prepared analogously to the procedure mentioned above:

| Compound No. | Structure | ESI (M + H) | HPLC Rt. in min. |
|---|---|---|---|
| "A64" | 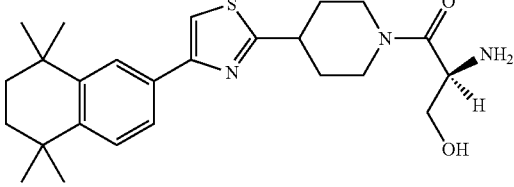 hydrochloride | 442 | |
| "A65" | 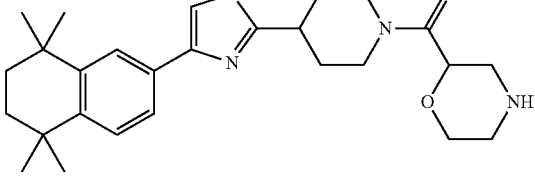 hydrochloride | 468 | |
| "A66" | 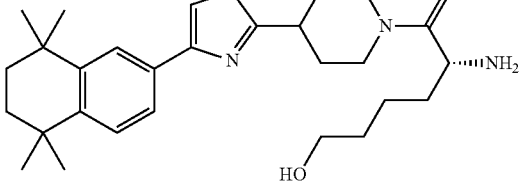 hydrochloride | 484 | |

-continued

| Compound No. | Structure | ESI (M + H) | HPLC Rt. in min. |
|---|---|---|---|
| "A67" | 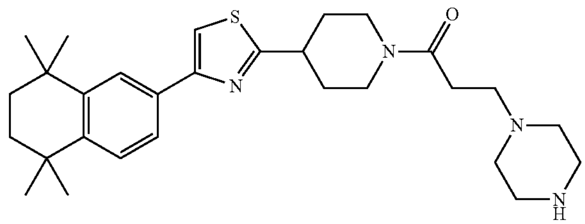 [SMILES: CC1(C)CCC(C)(C)c2cc(-c3csc(C4CCN(C(=O)CCN5CCNCC5)CC4)n3)ccc21] | 495 | |
| "A68" | 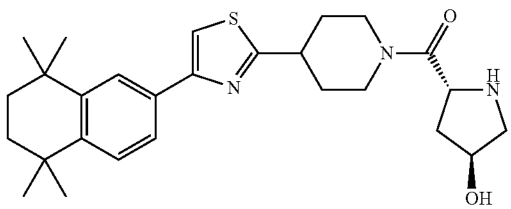 [SMILES: CC1(C)CCC(C)(C)c2cc(-c3csc(C4CCN(C(=O)[C@H]5C[C@H](O)CN5)CC4)n3)ccc21] | 468 | |
| "A69" | 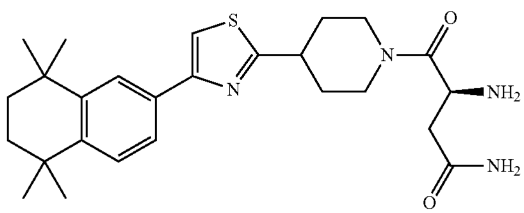 [SMILES: CC1(C)CCC(C)(C)c2cc(-c3csc(C4CCN(C(=O)[C@@H](N)CC(N)=O)CC4)n3)ccc21] | 469 | |
| "A70" | 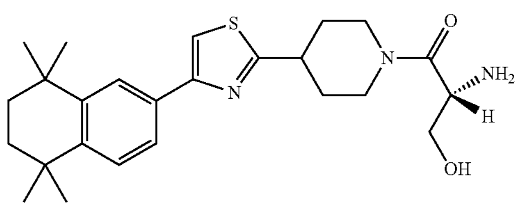 [SMILES: CC1(C)CCC(C)(C)c2cc(-c3csc(C4CCN(C(=O)[C@H](N)CO)CC4)n3)ccc21] | 442 | |
| "A81" | 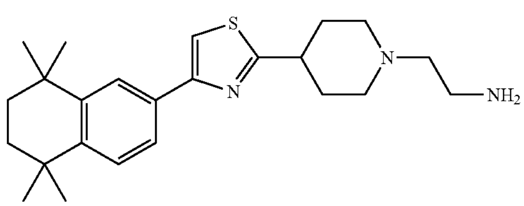 | 398 | 2.78 |
| | trifluoroacetate | | |
| "B16" | 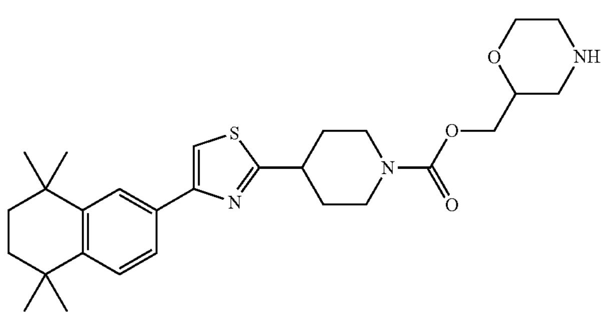 | 498 (M + H) | 3.21 |
| | trifluoroacetate | | |

Example 8

Preparation of (S)-2-amino-3-(3H-imidazol-4-yl)-1-{4-[4-(5,5,8,8-tetramethyl-5,6,7,8-tetrahydronaphthalen-2-yl)thiazol-2-yl]piperidin-1-yl}propan-1-one ("A82")

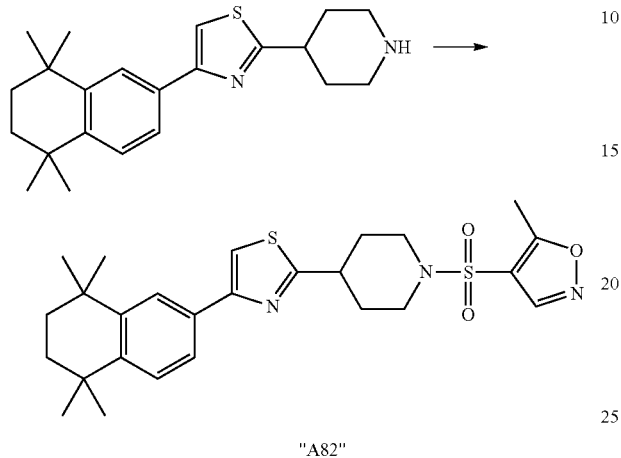

"A82"

255 µl (1.84 mmol) of triethylamine and 97 mg (0.51 mmol) of 5-methyl-4-isoxazolesulfonyl chloride are added to 200 mg (0.46 mmol) of 4-[4-(5,5,8,8-tetramethyl-5,6,7,8-tetrahydronaphthalen-2-yl)thiazol-2-yl]piperidine hydrobromide in 5 ml of dichloromethane. The reaction mixture is stirred at room temperature for 24 h. The reaction mixture is washed with saturated sodium hydrogencarbonate solution, the organic phase is dried over sodium sulfate and purified by column chromatography on silica gel. The product is crystallised from ether.

Yield: 98 mg of "A82", white solid; ESI: 500 (M+H), Rt.=3.83 min.

The following is obtained analogously

| Compound No. | Structure | ESI (M + H) | HPLC Rt. in min. |
|---|---|---|---|
| "A83" | 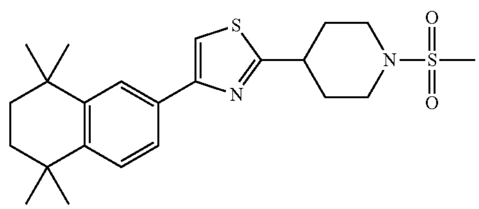 [SMILES: CC1(C)CCC(C)(C)c2cc(-c3csc(C4CCN(S(C)(=O)=O)CC4)n3)ccc21] | 433 | 3.84 |

Pharmacological Data
Met Kinase Inhibition (Enzyme Assay)

TABLE 1

| Compound No. | IC$_{50}$ |
|---|---|
| "A1" | C |
| "A2" | B |
| "A3" | C |
| "A4" | B |
| "A5" | B |
| "A6" | C |
| "A7" | C |
| "A8" | B |
| "A9" | A |
| "A10" | |
| "A11" | B |
| "A12" | B |
| "A13" | B |
| "A14" | B |
| "A15" | B |
| "A16" | B |
| "A17" | A |
| "A18" | B |
| "A19" | B |
| "A20" | A |
| "A21" | B |
| "A22" | A |
| "A23" | B |
| "A24" | B |
| "A25" | B |
| "A26" | B |
| "A27" | B |
| "A28" | A |
| "A29" | B |
| "A30" | A |
| "A31" | B |
| "A32" | A |
| "A33" | A |
| "A34" | A |
| "A35" | C |
| "A36" | B |
| "A37" | C |
| "A38" | A |
| "A40" | A |
| "A41" | B |
| "A42" | B |
| "A43" | B |
| "A44" | C |
| "A45" | C |
| "A46" | B |
| "A47" | B |
| "A48" | B |
| "A49" | C |
| "A50" | C |
| "A51" | B |
| "A52" | B |
| "A55" | C |
| "A57" | B |
| "A63" | B |
| "A64" | B |
| "A65" | A |
| "A66" | A |
| "A67" | C |

TABLE 1-continued

| Compound No. | IC$_{50}$ |
|---|---|
| "A68" | B |
| "A69" | B |
| "A70" | B |
| "A71" | B |
| "A72" | A |
| "A73" | A |
| "A74" | B |
| "A75" | A |
| "A76" | C |
| "A77" | B |
| "A78" | B |
| "A79" | B |
| "A80" | B |
| "A81" | A |
| "A82" | B |
| "A83" | C |
| "B1" | B |
| "B2" | A |
| "B3" | A |
| "B4" | A |
| "B5" | A |
| "B6" | A |
| "B7" | A |
| "B8" | B |
| "B9" | B |
| "B10" | A |
| "B11" | B |
| "B12" | B |
| "B13" | A |
| "B14" | B |
| "B15" | |
| "B16" | B |
| "C1" | A |
| "C2" | A |
| "C3" | A |
| "C5" | B |
| "C6" | A |
| "C7" | A |
| "C10" | B |
| "C11" | C |

IC$_{50}$: 10 nM-1 μM = A
1 μM-10 μM = B
>10 μM = C

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound, which is one of the following compounds

| No. | Structure and/or name |
|---|---|
| "A1" | 4-(2-Methyl-3-{4-[4-(5,5,8,8-tetramethyl-5,6,7,8-tetrahydro-naphthalen-2-yl)thiazol-2-yl]piperidin-1-yl}propyl)-morpholine |
| "A2" | 1'-Ethyl-4[4-(5,5,8,8-tetramethyl-5,6,7,8-tetrahydro-naphthalen-2-yl)thiazol-2-yl]-[1,3']bipiperidinyl |
| "A3" | (structure) |

| No. | Structure and/or name |
|---|---|
| "A4" | (structure) |
| "A5" | (structure) |
| "A6" | (structure) |
| "A7" | (structure) |
| "A8" | (structure) |
| "A9" | (structure) |
| "A10" | (structure) |
| "A11" | (structure) |
| "A12" | (structure) |
| "A13" | (structure) |
| "A14" | (structure) |
| "A15" | (structure) |
| "A16" | (structure) |
| "A17" | (structure) |
| "A18" | (structure) |
| "A19" | (structure) |

-continued
| No. | Structure and/or name |
|---|---|
| "A20" | 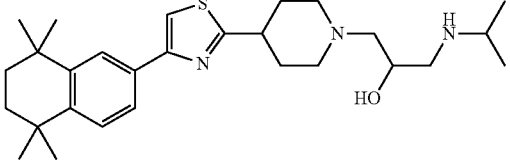 |
| "A21" | 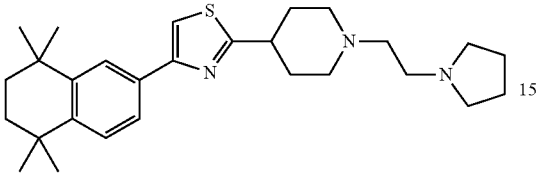 |
| "A22" | 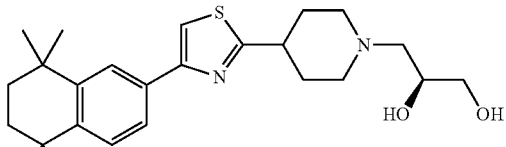 |
| "A23" | 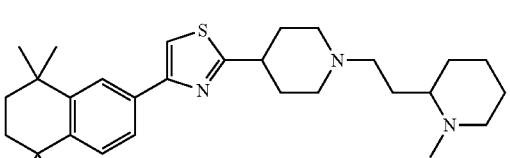 |
| "A24" | 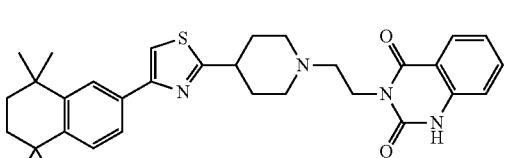 |
| "A25" | 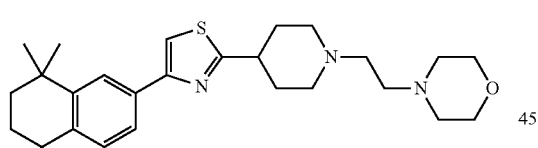 |
| "A26" | 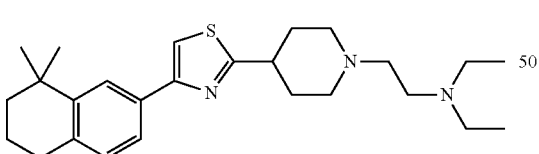 |
| "A27" | 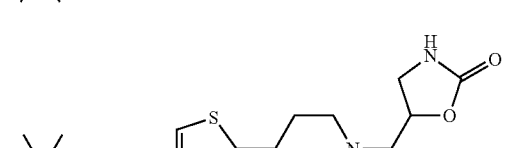 |
-continued
| No. | Structure and/or name |
|---|---|
| "A28" | 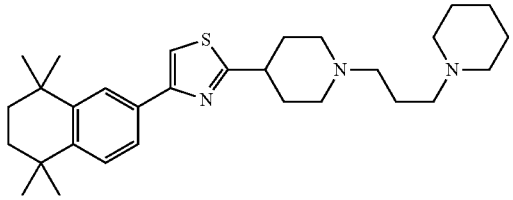 [SMILES: CC1(C)CCC(C)(C)c2cc(-c3csc(C4CCN(CCCN5CCCCC5)CC4)n3)ccc21] |
| "A29" | 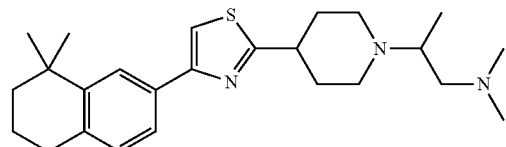 |
| "A30" | 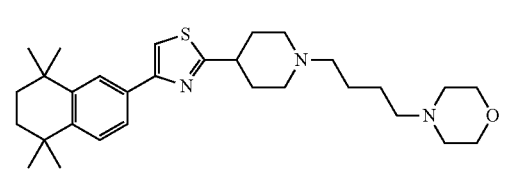 [SMILES: CC1(C)CCC(C)(C)c2cc(-c3csc(C4CCN(CCCCN5CCOCC5)CC4)n3)ccc21] |
| "A31" | 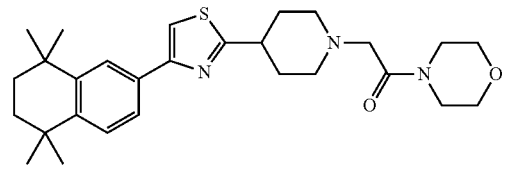 [SMILES: CC1(C)CCC(C)(C)c2cc(-c3csc(C4CCN(CC(=O)N5CCOCC5)CC4)n3)ccc21] |
| "A32" | 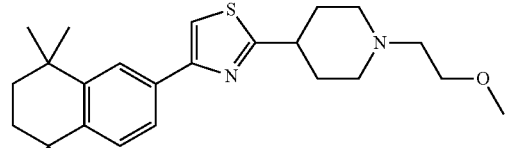 |
| "A35" | 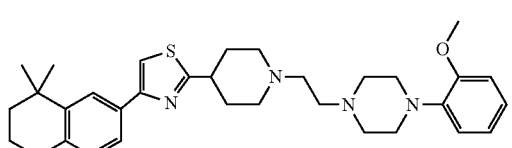 |
| "A36" | 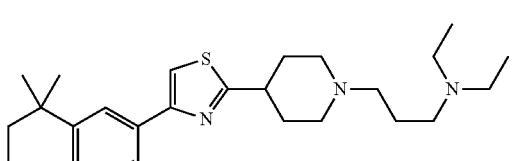 |
| "A37" | tert-Butyl (2-{4-[4-(5,5,8,8-tetramethyl-5,6,7,8-tetrahydro-naphthalen-2-yl)thiazol-2-yl]piperidin-1-yl}ethyl)carbamate |
| "A38" | 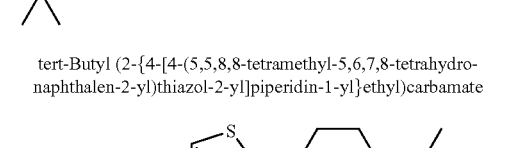 |

| No. | Structure and/or name |
|---|---|
| "A39" | 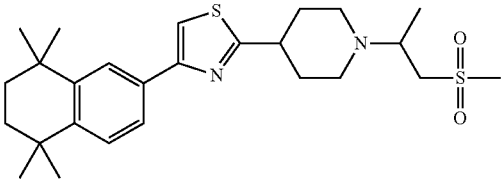 [SMILES: CC(CS(C)(=O)=O)N1CCC(c2nc(-c3ccc4c(c3)C(C)(C)CCC4(C)C)cs2)CC1] |
| "A40" | 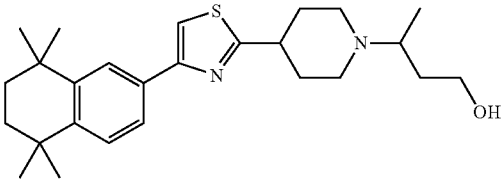 |
| "A41" | tert-Butyl (2-{4-[4-(5,5,8,8-tetramethyl-5,6,7,8-tetrahydro-naphthalen-2-yl)thiazol-2-yl]piperidin-1-yl}ethyl)carbamate |
| "A42" | 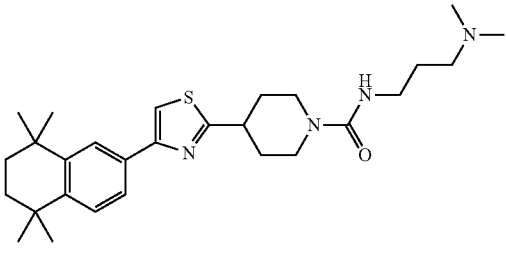 [SMILES: CN(C)CCCNC(=O)N1CCC(c2nc(-c3ccc4c(c3)C(C)(C)CCC4(C)C)cs2)CC1] |
| "A43" | 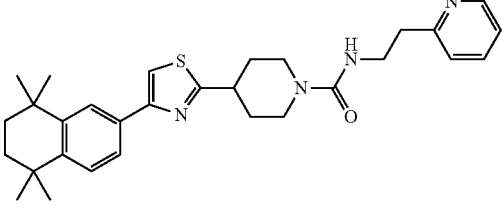 |
| "A44" | 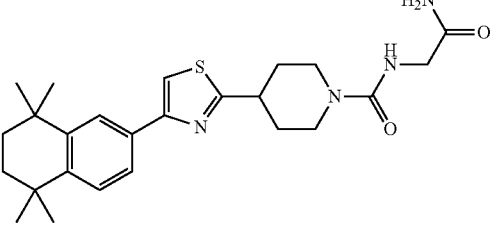 |
| "A45" | 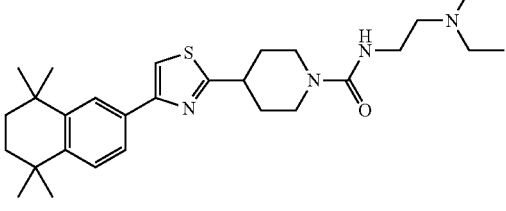 |

| No. | Structure and/or name |
|---|---|
| "A46" | 3-Methoxypropyl 4-[4-(5,5,8,8-tetramethyl-5,6,7,8-tetrahydronaphthalen-2-yl)thiazol-2-yl]piperidine-1-carboxylate |
| "A47" | 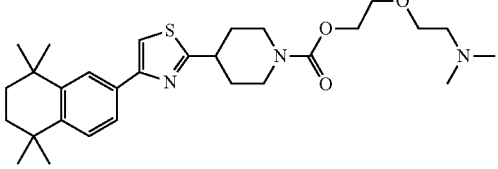 |
| "A48" | 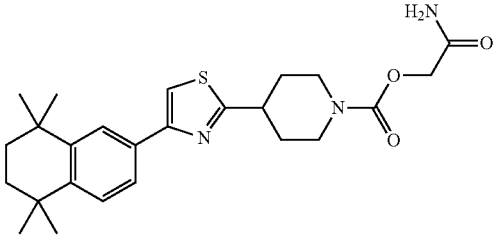 |
| "A49" | 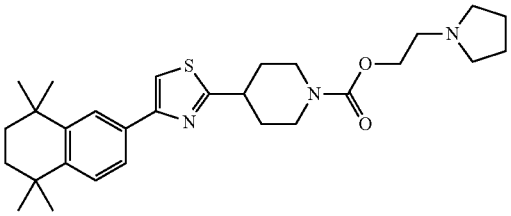 [SMILES: CC1(C)CCC(C)(C)c2cc(-c3csc(C4CCN(C(=O)OCCN5CCCC5)CC4)n3)ccc21] |
| "A50" | 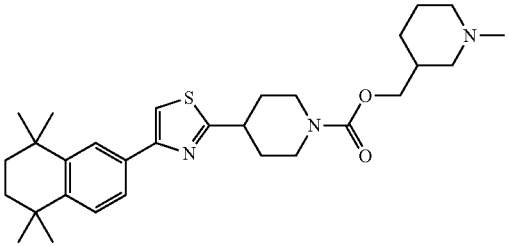 [SMILES: CN1CCCC(COC(=O)N2CCC(c3nc(-c4ccc5c(c4)C(C)(C)CCC5(C)C)cs3)CC2)C1] |
| "A51" | 2-Pyridin-4-yl-1-{4-[4-(5,5,8,8-tetramethyl-5,6,7,8-tetrahydronaphthalen-2-yl)thiazol-2-yl]piperidin-1-yl}ethanone |
| "A52" | 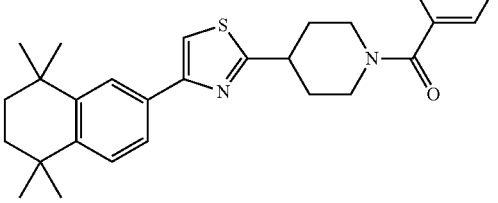 |
| "A53" | 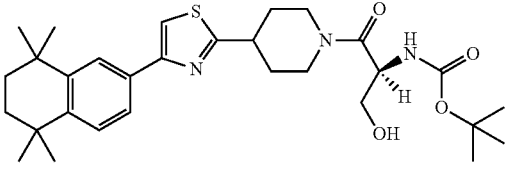 [SMILES: CC(C)(C)OC(=O)N[C@@H](CO)C(=O)N1CCC(c2nc(-c3ccc4c(c3)C(C)(C)CCC4(C)C)cs2)CC1] |

| No. | Structure and/or name |
|---|---|
| "A54" | 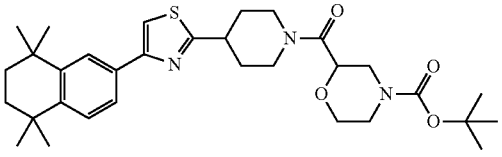 [SMILES: CC(C)(C)OC(=O)N1CCOC(C(=O)N2CCC(c3nc(-c4ccc5c(c4)C(C)(C)CCC5(C)C)cs3)CC2)C1] |
| "A55" | 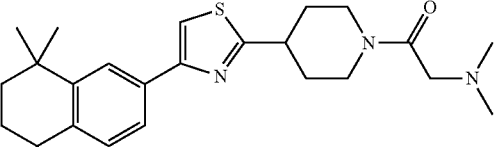 |
| "A56" | 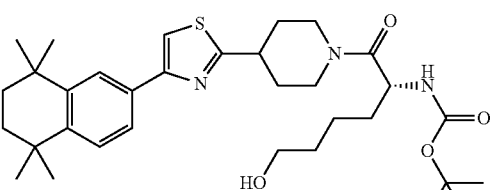 |
| "A57" | 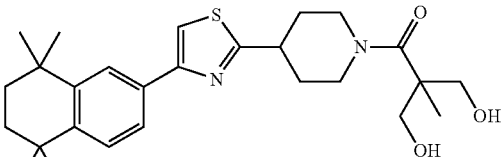 |
| "A58" | 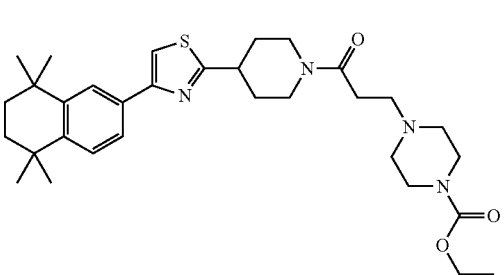 |
| "A59" | 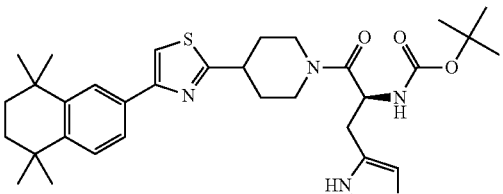 |
| "A60" | 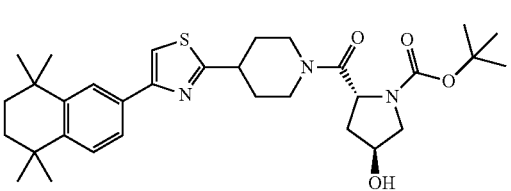 [SMILES: CC(C)(C)OC(=O)N1C[C@@H](O)C[C@@H]1C(=O)N1CCC(c2nc(-c3ccc4c(c3)C(C)(C)CCC4(C)C)cs2)CC1] |
| No. | Structure and/or name |
|---|---|
| "A61" | 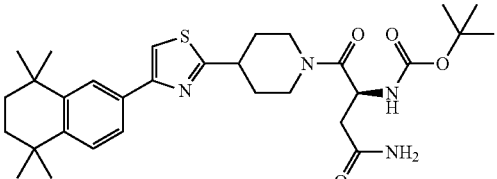 |
| "A62" | 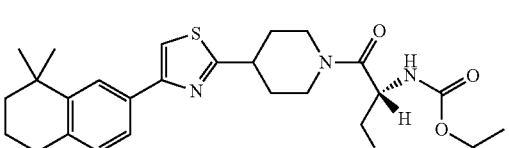 |
| "A63" | (S)-2-Amino-3-(3H-imidazol-4-yl)-1-{4-[4-(5,5,8,8-tetramethyl-5,6,7,8-tetrahydronaphthalen-2-yl)thiazol-2-yl]-piperidin-1-yl}propan-1-one |
| "A64" | 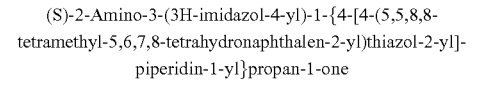 |
| "A65" | 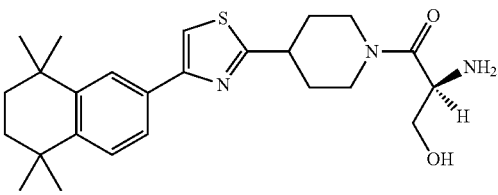 [SMILES: CC1(C)CCC(C)(C)c2cc(-c3csc(C4CCN(C(=O)[C@@H](N)CO)CC4)n3)ccc21] |
| "A66" | 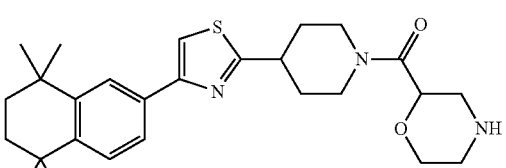 |
| "A67" | 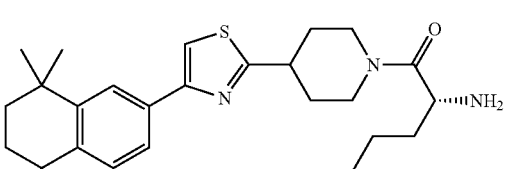 |
| "A68" | 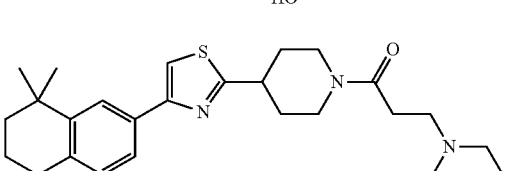 |

| No. | Structure and/or name | No. | Structure and/or name |
|---|---|---|---|
| "A69" | 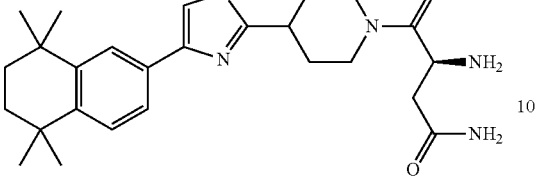 | "A76" | 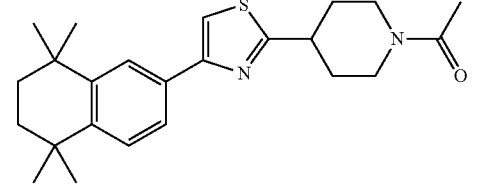 |
| "A70" | 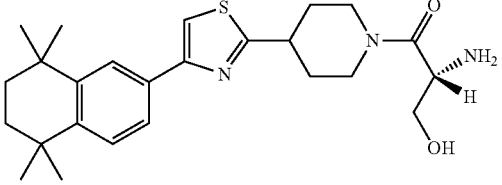 [SMILES: CC1(C)CCC(C)(C)c2cc(-c3csc(C4CCN(C(=O)[C@H](N)CO)CC4)n3)ccc21] | "A77" | 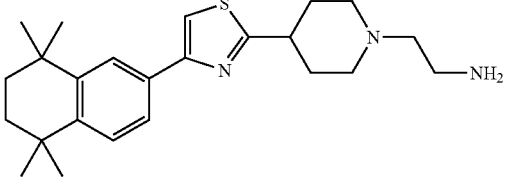 |
| "A71" | 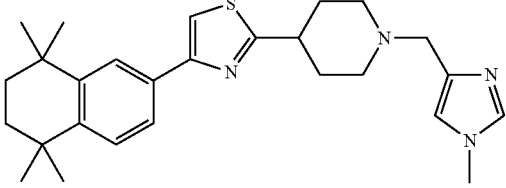 | "A78" | 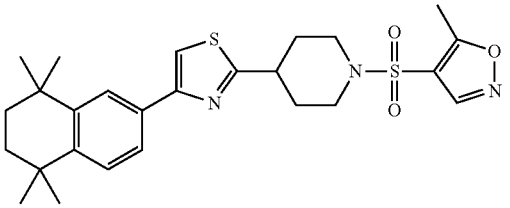 |
| "A72" | 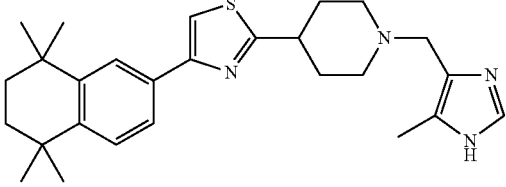 | "A79" | 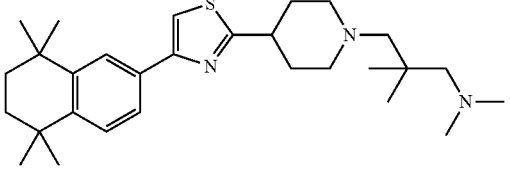 |
| "A73" | 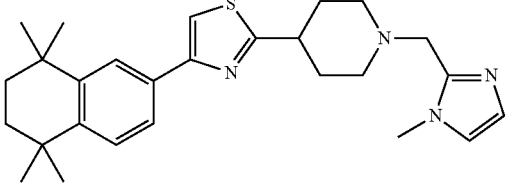 | "A80" | 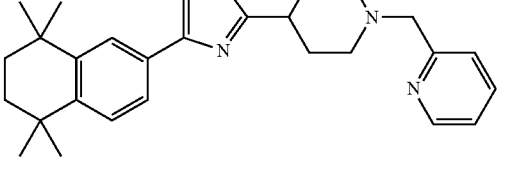 |
| "A74" | 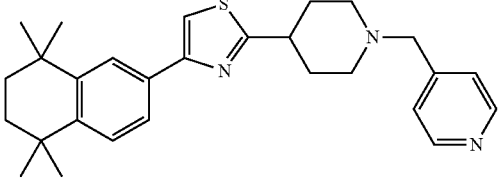 | "A81" | 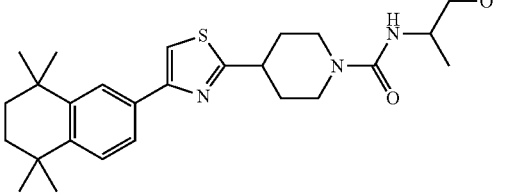 |
| "A75" | 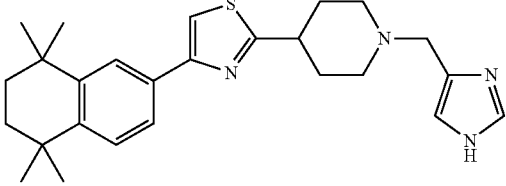 [SMILES: Cn1cnc(CN2CCC(c3nc(-c4ccc5c(c4)C(C)(C)CCC5(C)C)cs3)CC2)c1] | "A82" | 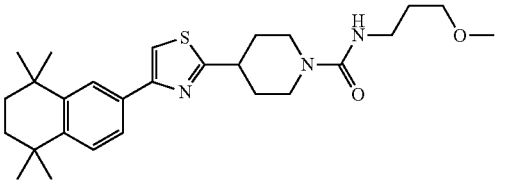 [SMILES: COCCCNC(=O)N1CCC(c2nc(-c3ccc4c(c3)C(C)(C)CCC4(C)C)cs2)CC1] |

| No. | Structure and/or name |
|---|---|
| "A83" | |
| "B1" | |
| "B2" | |
| "B3" | |
| "B4" | |
| "B5" | |
| "B6" | |
| "B7" | |
| "B8" | |
| "B9" | |
| "B10" | |
| "B11" | |
| "B12" | |
| "B13" | |
| "B14" | |
| "B15" | |

| No. | Structure and/or name |
|---|---|
| "B16" | 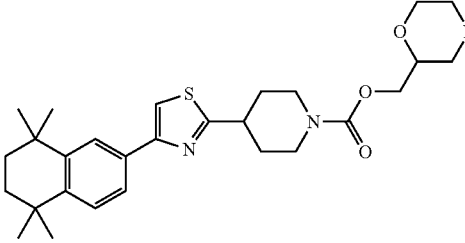 | or a pharmaceutically acceptable salt, tautomer or stereoisomer thereof.

2. A pharmaceutical composition comprising at least one compound according to claim 1 or a pharmaceutically acceptable salt, tautomer or stereoisomer thereof, and one or more pharmaceutically acceptable excipients and/or adjuvants.

3. A pharmaceutical composition comprising at least one compound according to claim 1 or a pharmaceutically acceptable salt, tautomer or stereoisomer thereof, and at least one further pharmaceutically active ingredient.

4. A kit comprising separate packs of
   (a) an effective amount of a compound according to claim 1 or a pharmaceutically acceptable salt, tautomer or stereoisomer thereof,
   and
   (b) an effective amount of a further pharmaceutically active ingredient.

\* \* \* \* \*